(12) United States Patent
Cid-Nunez et al.

(10) Patent No.: US 8,252,937 B2
(45) Date of Patent: Aug. 28, 2012

(54) 1,3-DISUBSTITUTED 4-(ARYL-X-PHENYL)-1H-PYRIDIN-2-ONES

(75) Inventors: Jose Maria Cid-Nunez, Toledo (ES); Andres Avelino Trabanco-Suarez, Toledo (ES); Gregor James MacDonald, Beerse (BE); Guillaume Albert Jacques Duvey, Geneva (CH); Robert Johannes Lutjens, Geneva (CH); Patrick Terry Finn, Geneva (CH)

(73) Assignees: Janssen Pharmaceuticals, Inc., Titusville, NJ (US); Addex Pharma S.A., Geneva (CH)

( * ) Notice: Subject to any disclaimer, the term of this patent is extended or adjusted under 35 U.S.C. 154(b) by 0 days.

(21) Appl. No.: 12/677,691

(22) PCT Filed: Sep. 12, 2008

(86) PCT No.: PCT/EP2008/007549
§ 371 (c)(1),
(2), (4) Date: Jun. 3, 2010

(87) PCT Pub. No.: WO2009/033702
PCT Pub. Date: Mar. 19, 2009

(65) Prior Publication Data
US 2010/0286206 A1    Nov. 11, 2010

(30) Foreign Application Priority Data
Sep. 14, 2007   (EP) .................... 07116388

(51) Int. Cl.
C07D 211/72 (2006.01)
A61K 31/44 (2006.01)
(52) U.S. Cl. ................. 546/290; 514/345
(58) Field of Classification Search .............. None
See application file for complete search history.

(56) References Cited

U.S. PATENT DOCUMENTS

| | | | |
|---|---|---|---|
| 4,066,651 A | 1/1978 | Brittain et al. | |
| 4,358,453 A | 11/1982 | Bristol et al. | |
| 4,550,166 A | 10/1985 | Moran et al. | |
| 5,032,602 A | 7/1991 | Fey et al. | |
| 5,236,917 A | 8/1993 | Dunlap et al. | |
| 5,356,911 A | 10/1994 | Muller-Gliemann et al. | |
| 5,371,074 A | 12/1994 | Dunlap et al. | |
| 5,374,513 A | 12/1994 | Ohzeki et al. | |
| 5,418,243 A * | 5/1995 | Angerbauer et al. | 514/345 |
| 5,498,774 A | 3/1996 | Mitsudera et al. | |
| 5,596,012 A | 1/1997 | Dunlap et al. | |
| 5,650,422 A | 7/1997 | Dunlap et al. | |
| 5,874,432 A | 2/1999 | Dunlap et al. | |
| 5,948,911 A | 9/1999 | Pamukcu et al. | |
| 6,110,920 A | 8/2000 | Rochas et al. | |
| 6,133,271 A | 10/2000 | Pamukcu et al. | |
| 6,607,563 B2 | 8/2003 | Ohashi et al. | |
| 7,456,289 B2 | 11/2008 | Hsieh et al. | |
| 7,572,807 B2 | 8/2009 | Li et al. | |
| 7,579,360 B2 | 8/2009 | Li et al. | |
| 2003/0171380 A1 | 9/2003 | Arvantis et al. | |
| 2005/0113283 A1 | 5/2005 | Solow-Cordero et al. | |
| 2007/0066582 A1 | 3/2007 | Herold et al. | |
| 2007/0213323 A1 | 9/2007 | Imogai et al. | |
| 2007/0275984 A1 | 11/2007 | Imogai et al. | |
| 2009/0031422 A1 | 1/2009 | Aaron et al. | |
| 2009/0124609 A1 | 5/2009 | Albrecht et al. | |
| 2009/0124612 A1 | 5/2009 | Albrecht et al. | |
| 2009/0203668 A1 | 8/2009 | Li et al. | |
| 2009/0318436 A1 | 12/2009 | Albrecht et al. | |
| 2010/0063092 A1 | 3/2010 | Cid-Nunez et al. | |
| 2010/0087487 A1 | 4/2010 | Cid-Nunez et al. | |
| 2010/0099715 A1 | 4/2010 | Cid-Nunez et al. | |

(Continued)

FOREIGN PATENT DOCUMENTS

CA    1019323    9/1977

(Continued)

OTHER PUBLICATIONS

Vippagunta et al., Adv. Drug Deliv. Rev. 48 (2001) pp. 3-26.*
Galici et al., "Biphenyl-indanone A, a Positive Allosteric Modulator of the Metabotropic Glutamate Receptor Subtype 2, Has Antipsychotic- and Anxiolytic-Like Effects in Mice," J Pharmacology and Experimental Therapeutics, 2006, 318, 173-185.

(Continued)

*Primary Examiner* — Janet Andres
*Assistant Examiner* — Heidi Reese
(74) *Attorney, Agent, or Firm* — Gardner Groff Greenwald & Villanueva, PC

(57) ABSTRACT

The present invention relates to novel compounds, in particular novel pyridinone derivatives according to Formula (I)

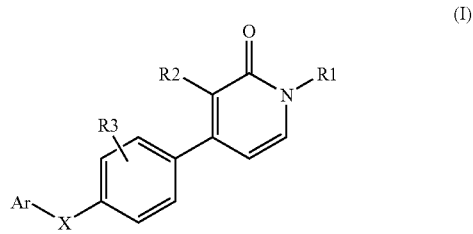

wherein all radicals are as defined in the application and claims. The compounds according to the invention are positive allosteric modulators of metabotropic receptors—subtype 2 ("mGluR2") which are useful for the treatment or prevention of neurological and psychiatric disorders associated with glutamate dysfunction and diseases in which the mGluR2 subtype of metabotropic receptors is involved. In particular, such diseases are central nervous system disorders selected from the group of anxiety, schizophrenia, migraine, depression, and epilepsy. The invention is also directed to pharmaceutical compositions and processes to prepare such compounds and compositions, as well as to the use of such compounds for the prevention and treatment of such diseases in which mGluR2 is involved.

6 Claims, No Drawings

U.S. PATENT DOCUMENTS

| | | | |
|---|---|---|---|
| 2010/0166655 A1* | 7/2010 | Imogai et al. | 424/9.1 |
| 2010/0240688 A1 | 9/2010 | Cid-Nunez et al. | |
| 2010/0240706 A1 | 9/2010 | Cid-Nunez et al. | |
| 2010/0286206 A1 | 11/2010 | Cid-Nunez et al. | |
| 2011/0275624 A1 | 11/2011 | Cid-Nunez et al. | |
| 2011/0306642 A1 | 12/2011 | Cid-Nunez | |

FOREIGN PATENT DOCUMENTS

| | | |
|---|---|---|
| CA | 2390948 | 12/2000 |
| CN | 1842532 | 10/2006 |
| CN | 102002040 | 4/2011 |
| EP | 154190 | 9/1985 |
| EP | 0373423 | 6/1990 |
| EP | 0430385 | 6/1991 |
| EP | 447118 | 9/1991 |
| EP | 0452002 | 10/1991 |
| EP | A10482939 | 4/1992 |
| EP | 0542059 | 5/1993 |
| EP | A1006112 | 6/2000 |
| EP | 1764099 | 3/2007 |
| GB | 1502312 | 3/1978 |
| JP | H02503317 | 10/1990 |
| JP | A2000072751 | 3/2000 |
| JP | 2002308882 | 10/2002 |
| JP | 2008509714 | 4/2008 |
| RU | C12143433 | 12/1999 |
| SU | 1509578 | 9/1989 |
| SU | 1796625 | 2/1993 |
| WO | 9504733 | 2/1995 |
| WO | 9511233 | 4/1995 |
| WO | 9710238 | 3/1997 |
| WO | 9721701 | 6/1997 |
| WO | 9811075 | 3/1998 |
| WO | 9817668 | 4/1998 |
| WO | 9824780 | 6/1998 |
| WO | 9832762 | 7/1998 |
| WO | 9962908 | 12/1999 |
| WO | 0003990 | 1/2000 |
| WO | 0034244 | 6/2000 |
| WO | 0129025 | 4/2001 |
| WO | 0132632 | 5/2001 |
| WO | WO 01/56990 | 8/2001 |
| WO | 0168097 | 9/2001 |
| WO | 0170731 | 9/2001 |
| WO | 0183481 | 11/2001 |
| WO | 0196308 | 12/2001 |
| WO | 0210807 | 2/2002 |
| WO | 0212236 | 2/2002 |
| WO | 0222598 | 3/2002 |
| WO | 0228837 | 4/2002 |
| WO | 02074025 | 9/2002 |
| WO | 02090333 | 11/2002 |
| WO | 02096318 | 12/2002 |
| WO | 02096363 | 12/2002 |
| WO | 03029209 | 4/2003 |
| WO | 03044021 | 5/2003 |
| WO | 03059884 | 7/2003 |
| WO | 03062392 | 7/2003 |
| WO | 03065994 | 8/2003 |
| WO | 03068230 | 8/2003 |
| WO | 03068750 | 8/2003 |
| WO | 2004017950 | 3/2004 |
| WO | 2004021984 | 3/2004 |
| WO | WO 2004/018386 | 3/2004 |
| WO | 2004031189 | 4/2004 |
| WO | 2004072025 | 8/2004 |
| WO | 2004078175 | 9/2004 |
| WO | 2004092123 | 10/2004 |
| WO | 2004092135 | 10/2004 |
| WO | WO 2004/092135 | 10/2004 |
| WO | 2005002585 | 1/2005 |
| WO | 2005021552 | 3/2005 |
| WO | 2005028445 | 3/2005 |
| WO | 2005040337 | 5/2005 |
| WO | 2005080356 | 9/2005 |
| WO | 2005097052 | 10/2005 |
| WO | 2006012622 | 2/2006 |
| WO | 2006015737 | 2/2006 |
| WO | 2006018727 | 2/2006 |
| WO | 2006020879 | 2/2006 |
| WO | WO 2006/014918 | 2/2006 |
| WO | WO 2006/015158 | 2/2006 |
| WO | WO 2006/030031 | 3/2006 |
| WO | WO 2006/030032 | 3/2006 |
| WO | 2006074041 | 7/2006 |
| WO | 2007031558 | 3/2007 |
| WO | 2007039439 | 4/2007 |
| WO | 2007059257 | 5/2007 |
| WO | 2007027669 | 8/2007 |
| WO | 2007103760 | 9/2007 |
| WO | 2007104783 | 9/2007 |
| WO | 2007113276 | 10/2007 |
| WO | 2007122258 | 11/2007 |
| WO | 2007135527 | 11/2007 |
| WO | 2007135529 | 11/2007 |
| WO | 2008006540 | 1/2008 |
| WO | 2008008539 | 1/2008 |
| WO | 2008012622 | 1/2008 |
| WO | 2008045393 | 4/2008 |
| WO | 2008051197 | 5/2008 |
| WO | 2008057855 | 5/2008 |
| WO | 2008076225 | 6/2008 |
| WO | 2008078091 | 7/2008 |
| WO | 2008078100 | 7/2008 |
| WO | 2008107125 | 9/2008 |
| WO | 2008107479 | 9/2008 |
| WO | 2008107480 | 9/2008 |
| WO | 2008107481 | 9/2008 |
| WO | 2008124085 | 10/2008 |
| WO | 2009033703 | 3/2009 |
| WO | 2009033704 | 3/2009 |
| WO | WO 2009/033702 | 3/2009 |
| WO | 2009045753 | 4/2009 |
| WO | 2009062676 | 5/2009 |
| WO | 2009091374 | 7/2009 |
| WO | 2009124609 | 10/2009 |
| WO | 2010022076 | 2/2010 |
| WO | 2010022081 | 2/2010 |
| WO | 2010025890 | 3/2010 |
| WO | 2010043396 | 4/2010 |
| WO | 2010063054 | 6/2010 |
| WO | 2010060589 | 7/2010 |
| WO | 2010089303 | 8/2010 |
| WO | 2010117926 | 10/2010 |
| WO | 2010130422 | 11/2010 |
| WO | 2010130423 | 11/2010 |
| WO | 2010130424 | 11/2010 |

OTHER PUBLICATIONS

Michael A. Benneyworth et al., "A Selective Positive Allosteric Modulator of Metabotropic Glutamate Receptor Subtype 2 Blocks a Hallucinogenic Drug Model of Psychosis," Molecular Pharmacology 72:477-484, 2007.

Mutel et al., "Characterization of (2S,2'R,3'R)-2-(2',3'-[3H]-Dicarboxycyclopropyl)glycine Binding in Rat Brain," J Neurochemistry, 71(6), 1998, 2558-2564.

Schaffhauser et al., "In Vitro Binding Characteristics of a New Selective Group II Metabotropic Glutamate Receptor Radioligand, [3H]LY354740, in Rat Brain," Mol Pharmacology, 53, 228-233, 1998.

Pin et al., "New perspectives for the development of selective metabotropic glutamate receptor ligands," European J of Pharmacology, 1999, 375, 277-294.

Schauffhauser et al., "Pharmacological Characterization and Identification of Amino Acids Involved in the Positive Modulation of Metabotropic Glutamate Receptor Subtype 2," Molecular Pharmacology, 2003, 4, 798-810.

Johnson et al., "Metabotropic glutamate 2 receptor potentiators: receptor modulation, frequency-dependent synaptic activity, and efficacy in preclinical anxiety and psychosis model(s)," Psychopharmacology, 2005, 179, 271-283.

Acta Chimica Slovencia, 2005, vol. 52, No. 4, pp. 391-397.

Azume et al., "Synthesis and reactions of 4-choloro-1, 2-dihydro-6-methyl-2-oxo-3-pyridinecarbonitrile", CA139:197340 (2003).

Bohme et al., "Darstellng and Umsetzungen von 3-Arylamino-2-halogencrotononitilen", Chem. Ber., 1976, 109, 2908-2913.
Braga et al. "Making Crystals from Crystals: A Green Route to Crystal Engineering and Polymorphism" Chem. Commun. 2005, 3635-3645.
Braish et al., "Construction of the (1x,5x,6x)-6-Amino-3-azabicyclo[3.1.0]hexane Ring System," Synlett, 1996, 1100-1102.
Brighty et al., "Synthesis of (1x,5x,6x)-6-Amino-3-azabicyclo[3.1.0]hexane, a Novel Achiral Diamine," Synlett, 1996, 1097-1099.
Chrostopoulos., "Allosteric Binding Sites on Cell-Sturcture Receptors: Novel Targets for Drug Discovery", Nature Rev., Mar. 2002, 1, 198-210.
Clark et al., "Synthesis of Thieno[2,3-d]pyrimidines from 4,6-Dichloropyrimidine-5-carbaldehydes", Journal Heterocyclic Chem, 1993, vol. 30, 1065-1072.
Cook et al. "Diethylaminoalkyl Ester Hydrochlorides of N-Alkyl-4-carbostyrilcarboxylic Acids", J Am. Chem. Soc., 1952, 74, 543-554.
DiMichelle et al. "The Natural Course of Schizophrenia and Psychopathological Predictors of Outcome", (Mar.-Apr. 2004), 37(2), pp. 98-104 (abstract).
Erlenmeyer et al., "Uber einige Derivate des 2-Aminothiazols", Helvetica Chim Acta, 1949, 35-38.
Fuentes et al., "Synthesis of Heterocyclic Compounds; XL. Regioselective. synthesis of 4-subtituted 2-Amino-5-Cyano-6-methoxy-3-benzenesulfonylpyridines", Synthesis, 1984, pp. 768-770.
Ghammamy et al., "Cetyltrimethylammonium Bromochromate: A New and Efficient Oxidant for Organic Substrates", Synthetic Communications, 2007, 37, 599-605.
Hamaguchi et al., "Effects of Hetero Atom Substituents in the decomposition of Pyrazolines: Abnormal Behavior of Methoxy Group Compared with Arylthio of Arylseleno Group.", Heterocycles, 1986, vol. 24, 2111-2115.
Haper, "Agonist-Stimulated [35S]GTPyS Binding," Current Protocols in Pharmacology, 1998, Unit 2.6, 1-10.
Harriman et al. "Synthesis of 4-Substituted 4-Arylpiperidines", Tetrahedron Letters, 2000, 41, 8853-8856.
Hughes, "Progress in the Mitsunobu Reaction. A Review," Organic Preparations and Procedures International, 1996, 127-164.
Hughes, "The Mitsunobu Reaction", Organinc Reactions, 1992, vol. 42, 335-656.
International Search Report dated Oct. 26, 2009 for international application No. PCT/EP2009/006326.
Kiselyov et al., "A one pot synthesis of polysubstituted inidazo[1,2-a]pyridines", Tetrahedron Letters, 2006, 47, 2941-2944.
Kitano et al., "Synthesis and antifouling activity of 3-isocyanotheonellin and its analogues", Jour Chem Soc Perkin Trans, 2002, 2251-2255, The Royal Society of Chemistry.
Klemm et al. "Chemistry of Thienopyridines. VIII. Substitution Products Derived from Thieno[2,3-b] pyridine 7-Oxide (1)", Journal of Heterocyclic Chemistry, 1970, 7(1), 81-89.
Larock, "Comprehensive Organic Transformations", VCH Publishers, 1989, 595-596.
Lee et al., "Benzylic Bromination of Alkylbenzenes with Sodium Bromate-Bromotrimethylsilane", Bull. Korean Chem. Soc, 1995, vol. 16, pp. 371-374.
Malames et al. "N-Substituted Spirosuccinimide, Spiropyridazine, Spiroazetidine, and Acetic Acid Aidose Reductase Inhibitiors Derived From Isoquinoline-1,3-dinoes. 2", J Med Chem., 1994, 37(13), 2059-2070.
McElvain et al. "Piperidine Derivatives. XXX. 1,4-Dialky1-4-arylpiperidines", J. Am. Chem. Soc, 1958, 80, 3915-3923.
Mongin et al. "Advances in the directed metallation of azines and diazines (pyridines, pyrimidines, pyrazines, pyridazines, quinolines, benzodiazines and carbolines). Part 1: Metallation of Pyridines, quinolines and carbolines", Tetrahedron, 2001, 57(19), 4059-4090.
Morrill et al., "Synthesis of 4-Arylpiperidines from 1-Benzyl-4piperidone: Application of the Sharpiro Reaction and Alkenylsilane Cross-coupling," Organic Letters, 2007, vol. 9, pp. 1505-1508.
Nakamura et al., "An Efficient Synthesis of Platelet-Activating Factor (PAF) J'IJ I-Qalkyl-2-~-(3-Isoxazolyl)-SN_Glycero-3-Phosphocholine, A New PAF Agonist. Utilization of the 3-Isoxazolyloxy Group As a Protected Hydroxyl." Tetrahedron Letters, 1990, vol. 31, 699-702.
Nakano et al. "1-Alkyl-3-phenylpyridinium 1-Alkyl-2(1H)-pyridone 3-Phenyl 5-Phenyl", Annual Report of Tohoku College of Pharmacy, 1998, 45, 145-148.
Nell et al., "Preparation of 4-amino-3,5-dicyano-2-thiopyridines as cardiovascular agents", CA149:32326 (2008).
Ojima et al., "Hydroformation of Fluoro Olefins, RfCH=CH2, Catalyzed by Group VIII Transition-Metal Catalysts. Crucial Factors for Extremly High Regioselectivity", Journal of American Chemical Society, 1987, 109, 7714-7720.
Potts et al. "1,2,4-Triazoles. XII. Derivatives of the s-Triazolo[4,3-a]pyridine Ring System", Journal of Organic Chemistry, 1966, 251-260.
Potts et al. "1,2,4-Trizoles. XXV. The Effect of Pyridine Substitution on the Isomerization of s-Triazolo [4,3-a] pyridines into s-Triazolo [1,5-a] pyridines (1)", J. Heterocycl. Chem., 1970, 7, 1019-1027.
Rani et al. "Thiazoline Analogues of Epiderstatin, New Inhibitiors of Cell Cycle of TsFT-210 Cells", Journal of Antibiotics, 1995, 48(10), 1179-1181.
Renslo et al., "Synthesis of Aza-, Oxa-, and Thiabicyclo[3.1.0]hexane Heterocycles from a Common Synthetic Intermediate," Organic Letters, 2005, vol. 7, No. 13, 2627-2630, American Chemical Society, USA.
Roma et al., "1,8-Naphthyridines VII. New substituted 5-amino[1,2,4]triazolo[4,3-a] [1,8]naphthyridine-6-carboxamides and their isosteric analogues, exhibiting notable anti-inflammatory and/or analgesic activities, but no acute gastrolesivity", European Journal of Medical Chemistry. 2008, 43, 1665-1680.
Seddon "Pseudopolymorph: A Polemic" Crystal Growth & Design, 4(6), 1087, 2004.
Shiba et al. "Synthesis and binding affinities of methylvesamicol analogs for the acetylcholine transporter and sigma receptor", Bioorganic and Medicinal Chemistry, 2006, 14, 2620-2626.
SIPO Office Action Jun. 30, 2010.
Stewart et al. "Discovery of Inhibitors of Cell Adhesion Molecule Expression in Human Endothelial Cell. 1. Selective Inhibition of ICAM-1 and E-Selectin Expression", J Med Chem, 2001, 44, 998-1002.
Turck et al. "Advances in the directed metallation of azines and diazines (pyridines, pyrimidines, pyrazines, pyridazines, quinolines, benzodiazines and carbolines). Part 2: Metallation of pyrimidines, pyrazines, pyridazines and benzodiazines", Tetrahedron, 2001, 57(21), 4489-4505.
Vilsmaier et al., "Diastereoselective Syntheses of N-Protected Derivatives of la,5a,6fi-6-Amino-3-azabicyclo [3.101] hexane; A Route to Trovafloxacin 6fl-Diastereomer," Synthesis, 1998, 739-744.
Wang et al. "A simple and effcient automatable one step synthesis of triazolopyridines form carboxylic acids", Tetrahedron Letters, 2007, 48, 2237-2240.
Watanbe et al. "Pd/P(t-Bu)3-Catalyzed Synthesis of Aromatic Amines", Journal of TOSOH Research, 1999, vol. 43, 38-50.
Wikipedia, "Allosteric Regulation", 2010, 1-4.
CA Office Action (Requisition b Examiner) mailed Apr. 23, 2010 in re co-pending Canadian Application No. 2,581,144, filed Sep. 16, 2005.
"Notification on the necessity to present additional materials" from the Eurasian Patent Organization dated Dec. 17, 2008.
Rosowsky et al., "2, 4-Diaminothieno [2.3-d]dipyrimidines as Antifolates and Antimalaris 3. Synthesis of 5, 6-Disubstitued Derivatives and Related Tetracyclic Analogs", Journal of Medicinal Chemistry, vol. 16, No. 3, 1973 pp. 191-194.
Benneyworth et al., "A Selective Positive Allosteric Modulator of Metabotropic Glutamate Receptor Subtype 2 Blocks a Hallucinogenic Drug Model of Psychosis," Mol. Pharmacol., 2007, 72, 477-484.
International Search Report and Combination Written Opinion of the International Searching Authority mailed Jul. 2, 2008 in re PCT/EP2008/052767, filed Mar. 7, 2008.
International Search Report and Combination Written Opinion of the International Searching Authority mailed Jun. 10, 2008 in re PCT/EP2008/052768, filed Mar. 7, 2008.

International Search Report and Combination Written Opinion of the International Searching Authority mailed Jun. 10, 2008 in re PCT/EP2008/052766, filed Mar. 7, 2008.

Eisa et al., "Synthesis of some novel tetrazole derivatives as potential antimicrobial agents," Pakistan J. of Scientific and Industrial Res, vol. 33, 1990, pp. 417-420.

Ruggero Galici, Carrie K. Jones, Kamondanai Hemstapat, Yi Nong, Nicholas G. Echemendia, Lilly C. Williams, Tomas de Paulis, and P. Jeffrey Conn, "Biphenyl-indanone A, a Positive Allosteric Modulator of the Metabotropic Glutamate Receptor Subtype 2, Has Antipsychotic- and Anxiolytic-Like Effects in Mice," JPET 318:173-185 2006.

The Synthesis of Perloline, 6-(3,4-Dimethoxyphenyl)-5-hydroxy-5,6-dihydrobenzo[c][2,7]napththyridin-4(3H)-one, Prager et al., Aust. J. Chem., 1983, 36, 1441-53.

A 'Biogenetic Like' Synthesis of Perloline, 6-(3,4-Dimethoxyphenyl)-5-hydroxy-5,6-dihydrobenzo[c][2,7]naphthyridin-4 (3H)-one, Duong, et al., Aust. J. Chem., 1983, 36, 1431-40.

Ring Transformation of Uracils to 3-Pyridones. Hydrolysis of 6-(2-Dimethylaminovinyl) Uracils, Senda et al., Heterocycles, vol. 9, No. 6, 1978 (6 pages).

Synthese von 3-Cyan-6-methyl-4-pyridyl-und 3-cyan-4-methyl-6-pyridyl-pyrid-2(1H)-onen und—thionen, Hanfeld, et al., Pharmazie 43 (1988), H.11, 762-764.

Studies with Polyfunctionally Substituted Heteroaromatics: New Routes for the Synthesis of Polyfunctionally Substituted Pyridines and 1,2,4-Triazolo[1,5-a]pyridines, Al-Omran, et al., Heteratom. Chemistry, vol. 6, No. 6, 1995, 545-551.

Diels-Alder Reactions of the Heterodiene System in 2(1H)-Pyrazinones, Tutonda, et al., Tetrahedron Letters, vol. 27, No. 22, pp. 2509-2512, 1986.

Cycloadditions of Cyanoketenes to Cinnamylideneamines and Benzylideneamines. Synthetic Scope, Stereochemistry, and Mechanism, Moore, et al., J. Org. Chem, 1985, 50, 4231-4238.

Reactions of Some 4-Methylene-4H-pyran Derivatives with Primary and Secondary Amines, VanAllan, et al., Journal of Heterocyclic Chemistry, vol. 7, Jun. 1970, 495-507.

A One-Step Preparation of Functionalized 3-Cyano-2-Pyridones, Jain, et al., Tetrahedron Letters, vol. 36, No. 19, pp. 3307-3310, 1995.

A new Synthetic Approach to the C-D Ring Portion of Streptonigrin Analogues, Kilama, et al., Journal of Heterocyclic Chemistry, vol. 27, Jul.-Aug. 1990, 1437-1440.

A Convenient Method for the Preparation of 2-Pyridone Derivatives, Kambe et al., 1977, vol. 12, pp. 841-842.

Torp-Ziegler Cyclization in the Synthesis of 3-Amino-4-Cyanopyrrole Derivatives, Ryndina, et al., Chemistry of Heterocyclic Compounds, vol. 36, No. 12, 2000, pp. 1409-1420.

Derivatives of 2-Pyridone, Wenner, et al., Journal of Organic Chemistry, 1946, vol. 11, pp. 751-759.

Alkylations at the Methyl or alpha-Methylene Group of 6- or 4-Alkyl-3-cyano-2(1)-pyridones through Dianions, Boatman, et al., Journal of Organic Chemistry, 1965, vol. 30 Pt 11, pp. 3593-3597.

Chemical Abstract, Yalyaheva et al., Heterocycles, p. 687, vol. 107, 1987.

Chemical Abstracts, Ershov et al., 1985, vol. 103, Pt 21, pp. 678.

Therapeutic potential of non-competitive, subtype-selective metabotropic glutamate receptor ligands, V. Mutel, Expert Opin. Ther. Patents (2002), 12 (12) p. 1845-1852.

Regulation of Neurotransmitter Release by Metabotropic Glutamate Receptors, Cartmell et al., J. Neurochem., p. 889-907, vol. 75, No. 3, 2000.

The selective group mGlu2/3 receptor agonist LY379268 suppresses REM sleep and fast EEG in the rat, Feinberg et al., Pharmacology, Biochemistry and Behavior 73 (2002) 467-474.

A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, Galici et al., J of Pharmacology and Experimental Therapeutics, p. 1181-1187, vol. 315, No. 3.

Activation of Group II Metabotropic Glutamate Receptors Inhibits Synaptic Excitation of the Subsantia Nigra Pars Reticulata, Bradley et al., J. of Neuroscience, May 1, 2000, 20(9):3085-3094.

Anxiolytic effects of a novel group II metabotropic glutamate receptor agonist (LY354740) in the fear-potentiated startle paradigm in humans, Grillon, et al., Psychopharmacology (2003) 168:446-454.

Anxiolytic and Side-Effect Profile of LY354740: A Potent, Highly Selective, Orally Active Agonist for Group II Metabotropic Glutamate Receptors, Helton et al., J. of Pharmacology and Experimental Therapeutics, p. 651-660, vol. 284, No. 2, 1997.

Excited by Glutamate, Science, p. 1866-1868, vol. 300, Jun. 20, 2003.

Benzazoles as allosteric potentiators of metabotropic glutamate receptor 2 (mGluR2): Efficacy in an animal model for schizophrenia, Govek et al., Bioorg. Med. Chem Lett. 15 (2005) 4068-4072.

Metabotropic glutamate 2 receptor potentiators: receptor modulation, frequency-dependent synaptic activity, and efficacy in preclinical anxiety and psychosis model(s), Johnson et al., Psychopharmacology (2005) 179: 271-283.

Discovery of Allosteric Potentiators for the Metabotropic Glutamate 2 Receptor: Synthesis and Subtype Selectivity of N-(4-(2-Methoxyphenoxy)phenyl)-N-(2,2,2-trifluorethylsulfonyl)pyrid-3-ylmethyl-amine, Johnson et al., J. Med. Chem. 2003, 46, 3189-3192.

Effects of metabotropic glutamate2/3 receptor agonist (LY544344/LY354740) on panic anxiety induced by cholecystokinin tetrapeptide in health humans: preliminary results, Kellner et al., Psychopharmacology (2005) 179: 310-315.

Allosteric modulators of metabotropic glutamate receptors: lessons learnt from mGlu1, mGlu2 and mGlu5 potentiators and antagonists, Johnson et al., Biochemical Society Transactions (2004) vol. 32, part 5, 881-887.

Selective, Non-Amino Acid Allosteric mGlu2 Receptor Potentiators Inhibit Dural Plasma Protein Extravasation; A Potential Role in the Treatment of Migraine, Johnson et al., Abstracts/Neuropharmacology 43 (2002) 291.

Khimia Geterotsiklicheskikh Soedinenii, 1985, vol. 5, PT 1985, 646-649.

Glutamate receptors: brain function and signal transduction, Nakanishi, et al., Brain Research Reviews 26 (1998) 230-235.

Activation of Metabotropic Glutamate Receptor-1 Accelerates NMDA Receptor Trafficking, Lan et al., Abstracts/Neuropharmacology 43 (2002) 294.

Glutamate metabotropic receptors as targets for drug therapy in epilepsy, Moldrich et al., European Journal of Pharmacology 476 (2003) 3-16.

Metabotropic glutamate receptor 2 modulates excitatory synaptic transmission in the rat globus pallidus, Poisik, et al., Neuropharmacology 49 (2005) 57-69.

Pharmacological Characterization and Identification of Amino Acids Involved in the Positive Modulation of Metabotropic Glutamate Receptor Subtype 2, Schaffhauser et al., Mol. Pharmacol 64:798-810, 2003, vol. 64, No. 4.

The metabotropic glutamate receptor 5 antagonist MPEP and the mGluR2 agonist LY379268 modify disease progression in a transgenic mouse model of Huntington's disease, Schiefer, et al., Brain Research 1019 (2004) 246-254.

Phenyl-tetrazolyl Acetophenones: Discovery of Positive Allosteric Potentiators for the Metabotropic Glutamate 2 Receptor, Pinkerton, et al., J. Med. Chem 2004, 47, 4595-4599.

Pharmacological agents acting at subtypes of metabotropic glutamate receptors, Schoepp, Neuropharmacology 38 (1999) 1431-1476.

Group II mGluR receptor agonists are effective in persistent and neuropathic pain models in rats, Simmons, et al., Pharmacology, Biochemistry and Behavior 73 (2002) 419-427.

Preclinical Pharmacology of mGlu2/3 Receptor Agonists: Novel Agents for Schizophrenia?, Schoepp et al., CNS & Neurological Disorders, 2002, 1, 215-225.

* cited by examiner

1,3-DISUBSTITUTED 4-(ARYL-X-PHENYL)-1H-PYRIDIN-2-ONES

IN THE CROSS-REFERENCE TO RELATED APPLICATIONS

This application claims priority to European Application No. 07116388.5, filed Sep. 14, 2007, which is hereby incorporated herein by reference in its entirety for all purposes.

FIELD OF THE INVENTION

The present invention relates to novel pyridinone-derivatives which are positive allosteric modulators of the metabotropic glutamate receptor subtype 2 ("mGluR2") and which are useful for the treatment or prevention of neurological and psychiatric disorders associated with glutamate dysfunction and diseases in which the mGluR2 subtype of metabotropic receptors is involved. The invention is also directed to pharmaceutical compositions comprising such compounds, to processes to prepare such compounds and compositions, and to the use of such compounds for the prevention or treatment of neurological and psychiatric disorders and diseases in which mGluR2 is involved.

BACKGROUND OF THE INVENTION

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptors channels (iGluRs), and the NMDA, AMPA and kainate receptors which are responsible for fast excitatory transmission.

In addition, glutamate activates metabotropic glutamate receptors (mGluRs) which have a more modulatory role that contributes to the fine-tuning of synaptic efficacy.

Glutamate activates the mGluRs through binding to the large extracellular amino-terminal domain of the receptor, herein called the orthosteric binding site. This binding induces a conformational change in the receptor which results in the activation of the G-protein and intracellular signalling pathways.

The mGluR2 subtype is negatively coupled to adenylate cyclase via activation of Gαi-protein, and its activation leads to inhibition of glutamate release in the synapse. In the central nervous system (CNS), mGluR2 receptors are abundant mainly throughout cortex, thalamic regions, accessory olfactory bulb, hippocampus, amygdala, caudate-putamen and nucleus accumbens.

Activating mGluR2 was shown in clinical trials to be efficacious to treat anxiety disorders. In addition, activating mGluR2 in various animal models was shown to be efficacious, thus representing a potential novel therapeutic approach for the treatment of schizophrenia, epilepsy, addiction/drug dependence, Parkinson's disease, pain, sleep disorders and Huntington's disease.

To date, most of the available pharmacological tools targeting mGluRs are orthosteric ligands which activate several members of the family as they are structural analogs of glutamate.

A new avenue for developing selective compounds acting at mGluRs is to identify compounds that act through allosteric mechanisms, modulating the receptor by binding to a site different from the highly conserved orthosteric binding site.

Positive allosteric modulators of mGluRs have emerged recently as novel pharmacological entities offering this attractive alternative. Various compounds have been described as mGluR2 positive allosteric modulators. WO2004/092135 (NPS & Astra Zeneca), WO2004/018386, WO2006/014918 and WO2006/015158 (Merck), WO2001/56990 (Eli Lilly) and WO2006/030032 (Addex & Janssen Pharmaceutica) describe respectively phenyl sulfonamide, acetophenone, indanone, pyridylmethyl sulfonamide and pyridinone derivatives as mGluR2 positive allosteric modulators. None of the specifically disclosed compounds therein are structurally related to the compounds of the present invention.

It was demonstrated that such compounds do not activate the receptor by themselves. Rather, they enable the receptor to produce a maximal response to a concentration of glutamate which by itself induces a minimal response. Mutational analysis has demonstrated unequivocally that the binding of mGluR2 positive allosteric modulators does not occur at the orthosteric site, but instead at an allosteric site situated within the seven transmembrane region of the receptor.

Animal data are suggesting that positive allosteric modulators of mGluR2 have effects in anxiety and psychosis models similar to those obtained with orthosteric agonists. Allosteric modulators of mGluR2 were shown to be active in fear-potentiated startle, and in stress-induced hyperthermia models of anxiety. Furthermore, such compounds were shown to be active in reversal of ketamine- or amphetamine-induced hyperlocomotion, and in reversal of amphetamine-induced disruption of prepulse inhibition of the acoustic startle effect models of schizophrenia (J. Pharmacol. Exp. Ther. 2006, 318, 173-185; Psychopharmacology 2005, 179, 271-283).

Recent animal studies further reveal that the selective positive allosteric modulator of metabotropic glutamate receptor subtype 2 biphenyl-indanone (BINA) blocks a hallucinogenic drug model of psychosis, supporting the strategy of targeting mGluR2 receptors for treating glutamatergic dysfunction in schizophrenia (Mol. Pharmacol. 2007, 72, 477-484).

Positive allosteric modulators enable potentiation of the glutamate response, but they have also been shown to potentiate the response to orthosteric mGluR2 agonists such as LY379268 or DCG-IV. These data provide evidence for yet another novel therapeutic approach to treat above mentioned neurological and psychiatric diseases involving mGluR2, which would use a combination of a positive allosteric modulator of mGluR2 together with an orthosteric agonist of mGluR2.

Compounds in the present invention are superior to the compounds described in the EP application No. 07103654 in that they show higher in vitro potency and improved in vivo pharmacokinetics, particularly enhanced brain levels.

DETAILED DESCRIPTION OF THE INVENTION

The present invention relates to compounds having metabotropic glutamate receptor 2 modulator activity, said compounds having the Formula (I)

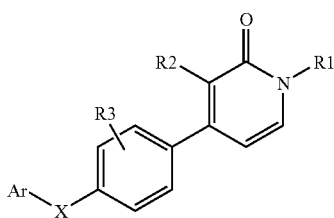

(I)

and the stereochemically isomeric forms thereof, wherein $R^1$ is $C_{1-6}$alkyl; or $C_{1-3}$alkyl substituted with $C_{3-7}$cycloalkyl, phenyl, or phenyl substituted with halo, trifluoromethyl or trifluoromethoxy;

$R^2$ is halo, trifluoromethyl, $C_{1-3}$alkyl or cyclopropyl;

$R^3$ is hydrogen or halo;

X is O, S, SO, $SO_2$, or $CF_2$; and

Ar is unsubstituted phenyl; unsubstituted pyridinyl; or phenyl or pyridinyl substituted with one or two substituents selected from the group consisting of halo, $C_{1-3}$alkyl, $C_{1-3}$alkoxy, trifluoromethyl, hydroxy$C_{1-3}$ alkyl and $(CH_2)_n$—$CO_2H$, wherein n=0, 1, or 2; and the pharmaceutically acceptable salts and solvates thereof, provided that when $R^3$ is 2'-fluoro then Ar is not 3-pyridinyl substituted with one or two $C_{1-3}$alkyl substituents.

In one embodiment, the invention relates to a compound according to Formula (I) or a stereochemically isomeric form thereof, wherein $R^1$ is 1-butyl, 2-methyl-1-propyl, 3-methyl-1-butyl, (cyclopropyl)methyl or 2-(cyclopropyl)-1-ethyl;

$R^2$ is chloro or trifluoromethyl;

$R^3$ is hydrogen, chloro or fluoro;

X is O; and

Ar is pyridinyl substituted with at least one methyl, or phenyl substituted with COOH or hydroxyC1-3 alkyl; or a pharmaceutically acceptable salt or solvate thereof.

In one embodiment, the invention relates to a compound according to Formula (I) or a stereochemically isomeric form thereof, wherein $R^1$ is 1-butyl, 3-methyl-1-butyl, (cyclopropyl)methyl or 2-(cyclopropyl)-1-ethyl;

$R^2$ is chloro;

$R^3$ is chloro or fluoro;

X is O; and

Ar is 2-methylpyridin-4-yl, 2-methylpyridin-3-yl or 2,6-dimethylpyridin-4-yl, or a pharmaceutically acceptable salt or solvate thereof.

In one embodiment, the invention relates to a compound according to formula (I) or a stereochemically isomeric form thereof wherein R' is 1-butyl, 3-methyl-1-butyl, (cyclopropyl)methyl or 2-(cyclopropyl)-1-ethyl;

$R^2$ is chloro;

$R^3$ is 3'-chloro or 3'-fluoro;

X is O; and

Ar is 2-methylpyridin-4-yl, 2-methylpyridin-3-yl or 2,6-dimethylpyridin-4-yl, or a pharmaceutically acceptable salt or solvate thereof.

The notation $C_{1-3}$ alkyl as a group or part of a group defines a saturated, straight or branched, hydrocarbon radical having from 1 to 3 carbon atoms, such as methyl, ethyl, 1-propyl and 1-methylethyl.

The notation $C_{1-6}$alkyl as a group or part of a group defines a saturated, straight or branched, hydrocarbon radical having from 1 to 6 carbon atoms such as methyl, ethyl, 1-propyl, 1-methylethyl, 1-butyl, 2-methyl-1-propyl, 3-methyl-1-butyl, 1-pentyl, 1-hexyl and the like.

The notation $C_{3-7}$cycloalkyl defines a saturated, cyclic hydrocarbon radical having from 3 to 7 carbon atoms, such as cyclopropyl, cyclobutyl, cyclopentyl, cyclohexyl and cycloheptyl.

The notation halo or halogen as a group or part of a group is generic for fluoro, chloro, bromo, iodo.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable salts are defined to comprise the therapeutically active non-toxic acid addition salt forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely said salt forms can be converted into the free base form by treatment with an appropriate base.

The compounds according to Formula (I) containing acidic protons may also be converted into their therapeutically active non-toxic base salt forms by treatment with appropriate organic and inorganic bases. Appropriate base salt forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salt forms can be converted into the free acid forms by treatment with an appropriate acid.

The term solvate comprises the solvent addition forms as well as the salts thereof, which the compounds of formula (I) are able to form. Examples of such solvent addition forms are e.g. hydrates, alcoholates and the like.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. The invention also embraces each of the individual isomeric forms of the compounds of Formula (I) and their salts and solvates, substantially free, i.e. associated with less than 10%, preferably less than 5%, in particular less than 2% and most preferably less than 1% of the other isomers. Thus, when a compound of formula (I) is for instance specified as (R), this means that the compound is substantially free of the (S) isomer. Stereogenic centers may have the R- or S-configuration; substituents on bivalent cyclic (partially) saturated radicals may have either the cis- or trans-configuration.

Following CAS nomenclature conventions, when two stereogenic centers of known absolute configuration are present in a compound, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the compound has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{3}H$, $^{11}C$ and $^{18}F$.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

A. PREPARATION OF THE FINAL COMPOUNDS

Experimental Procedure 1

The compounds according to Formula (I) can be prepared by reacting an intermediate of Formula (II) with a compound of Formula (III) according to reaction scheme (1), a reaction that is performed in a suitable reaction-inert solvent, such as, for example, 1,4-dioxane or mixtures of inert solvents such as, for example, 1,4-dioxane/DMF, in the presence of a suitable base, such as, for example, aqueous $NaHCO_3$ or $Na_2CO_3$, a Pd-complex catalyst such as, for example, tetrakis(triphenylphosphine)palladium(0), heating for a suitable period of time that allows the completion of the reaction either under conventional heating or under microwave irradiation, typically heating the reaction mixture at 150° C. under microwave irradiation for 10 min. In reaction scheme (1), all variables are defined as in Formula (I) and Y is a group suitable for Pd mediated coupling with boronic acids or boronic esters, such as, for example, a halogen or triflate and $R_4$ and $R_5$ may be hydrogen or alkyl, or may be taken together to form for example the bivalent radical of formula —$CH_2CH_2$—, —$CH_2CH_2CH_2$—, or —$C(CH_3)_2C(CH_3)_2$—. Such intermediates (II) and (III) may be prepared according to reaction schemes (2) to (15). The transformations of different functional groups present in the final compounds, into other functional groups according to Formula (I), can be performed by synthesis methods well known by the person skilled in the art.

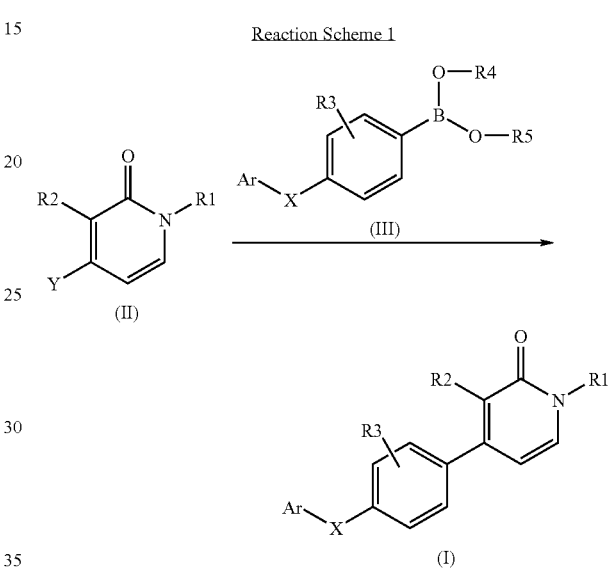

Reaction Scheme 1

B. PREPARATION OF THE INTERMEDIATES

Experimental Procedure 2

Intermediates of Formula (II-a) wherein Y represents halogen (Halo) can be prepared by reacting an intermediate of Formula (IV) with a suitable halogenating agent such as, for example, phosphorus oxybromide, a reaction that is performed in a suitable reaction-inert solvent such as, for example, DMF, at a moderately elevated temperature such as, for example, 110° C. In reaction scheme (2), all variables are defined as in Formula (I).

Reaction Scheme 2

Experimental Procedure 3

Intermediates of Formula (II-b) wherein Y represents a triflate can be prepared by reacting an intermediate of Formula (IV) with triflic anhydride (also called trifluoromethanesulfonic anhydride), a reaction that is performed in a suitable reaction-inert solvent such as, for example, dichloromethane, in the presence of a base such as, for example, pyridine at a low temperature such as, for example, −78° C. In reaction scheme (3), all variables are defined as in Formula (I).

Reaction Scheme 3

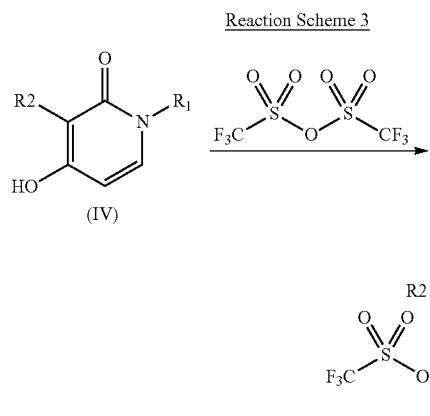

Experimental Procedure 4

Intermediates of Formula (IV-a) wherein $R^2$ represents halogen, can be prepared by reacting an intermediate of Formula (V) with a N-halosuccinimide reagent, such as N-chlorosuccinimide, N-bromosuccinimide or N-iodosuccinimide, according to reaction scheme (4). This reaction is performed in a suitable reaction-inert and aprotic solvent, such as, for example, dichloromethane or 1,2-dichloroethane, stirring the reaction mixture at a suitable temperature, typically at room temperature, for the required time to achieve completion of the reaction. In reaction scheme (4), variable R' is defined as in Formula (I).

Reaction Scheme 4

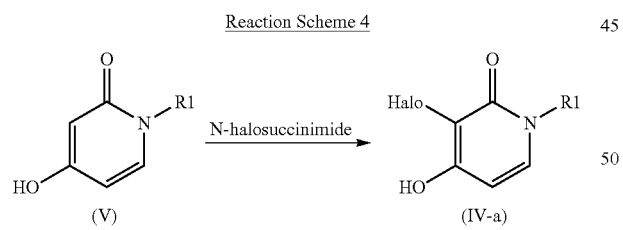

Experimental Procedure 5

Intermediates of Formula (IV-b) wherein $R^2$ represents trifluoromethyl, $C_{1-3}$alkyl or cyclopropyl, can be prepared by hydrogenolysis of intermediates of Formula (VI), in a suitable reaction-inert solvent such as, for example, ethanol, in the presence of a catalyst such as, for example, 10% palladium on activated carbon, for a period of time that ensures the completion of the reaction, typically at room temperature and 1 atmosphere of hydrogen for 2 hours. In reaction scheme (5), variable $R^1$ is defined as in Formula (I).

Reaction Scheme 5

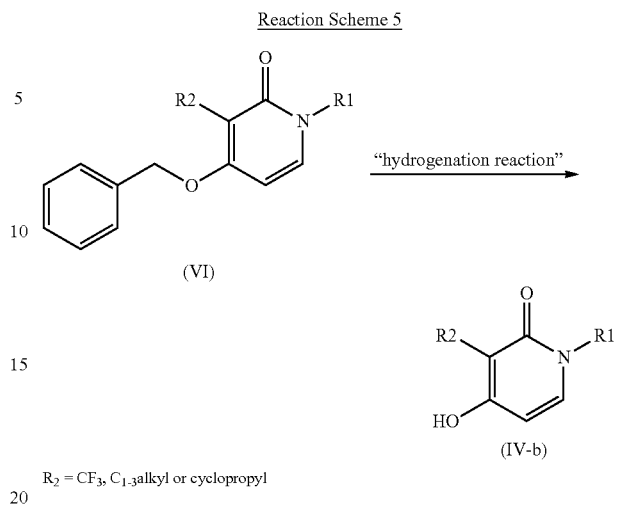

$R_2 = CF_3, C_{1-3}alkyl$ or cyclopropyl

Experimental Procedure 6

Intermediates of Formula (V) can be prepared by hydrogenolysis of intermediates of Formula (VII), in a suitable reaction-inert solvent such as, for example, ethanol, in the presence of a catalyst such as, for example, 10% palladium on activated carbon, for a period of time that ensures the completion of the reaction, typically at room temperature and 1 atmosphere of hydrogen for 2 hours. In reaction scheme (6), variable $R^1$ is defined as in Formula (I).

Reaction Scheme 6

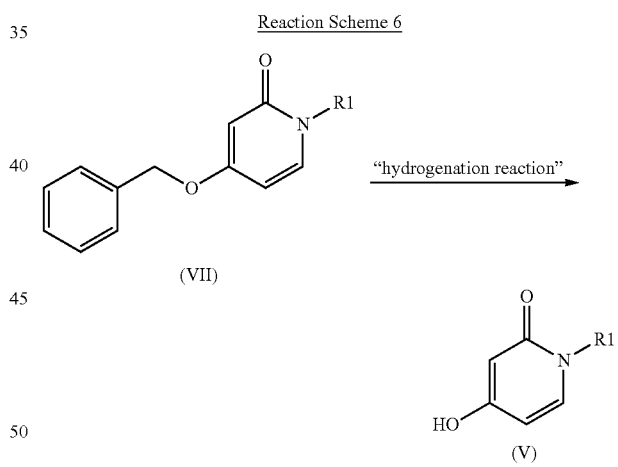

Experimental Procedure 7

Intermediates of Formula (VII) can be prepared by art known procedures by reacting commercially available 4-benzyloxy-1H-pyridin-2-one [CAS: 53937-02-3] with a commercially available alkylating agent of Formula (VIII), in which Z is a leaving group, using a base such as, for example, $K_2CO_3$, and, optionally an iodine salt such as, for example, KI, in an inert solvent such as, for example, acetonitrile or DMF, at a moderately high temperature such as, for example, 80-120° C., for a suitable period of time that allows the completion of the reaction, for example 16 hours. In reaction scheme (7), variable $R^1$ is defined as in Formula (I) and Z is a leaving group such as, for example, halogen.

Reaction Scheme 7

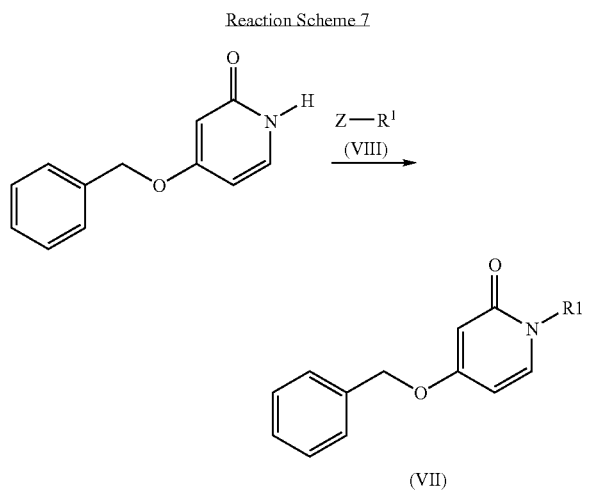

Experimental Procedure 8

Intermediates of Formula (VI-a) wherein $R^2$ is halogen can be prepared by reacting an intermediate of Formula (VII) with a commercially available N-halosuccinimide, such as N-chloro-(NCS), N-bromo- (NBS) or N-iodosuccinimide (NIS), in a suitable reaction-inert solvent such as, for example, DMF, dichloromethane or acetic acid, typically at room temperature for 1 to 24 hours. In reaction scheme (8), variable $R^1$ is defined as in Formula (I).

Reaction Scheme 8

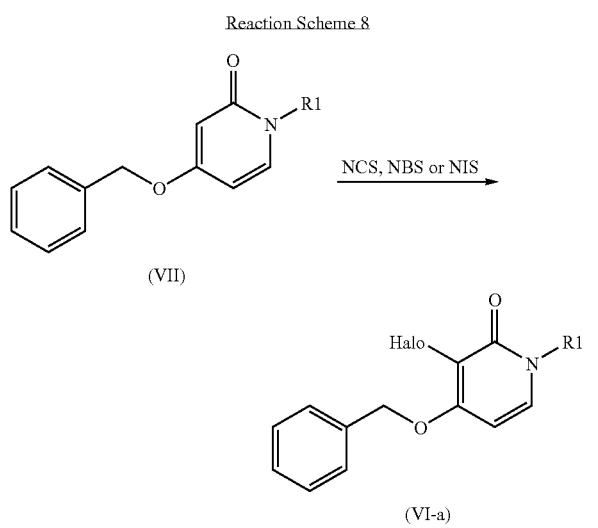

Experimental Procedure 9

Intermediates of Formula (VI-b) wherein $R^2$ represents $CF_3$ can be prepared by reacting an intermediate of Formula (VI-a) wherein halogen represents iodine, with commercially available methyl 2,2-difluoro-2-(fluorosulfonyl)acetate, in a suitable reaction-inert solvent such as, for example, DMF, in presence of a suitable copper salt such as copper(I) iodide, heating for a suitable period of time that allows the completion of the reaction, for example at 100° C. for 5 hours. In reaction scheme (9), variable R' is defined as in Formula (I).

Reaction Scheme 9

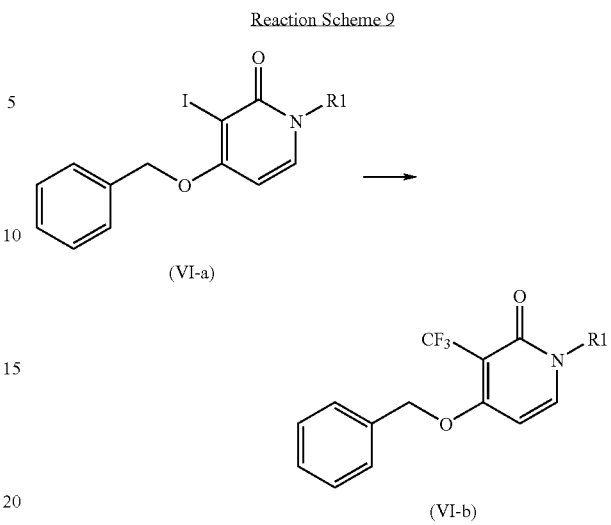

Experimental Procedure 10

Intermediates of Formula (VI-c) wherein $R^2$ is $C_{1-3}$alkyl or cyclopropyl can be prepared by reacting an intermediate of Formula (VI-a) with a $C_{1-3}$alkyl- or cyclopropyl-boronic acid derivative, such as cyclopropylboronic acid or methylboronic acid, in a suitable reaction-inert solvent such as, for example, 1,4-dioxane, in the presence of a suitable palladium catalyst-complex such as, for example, [1,1'-bis(diphenylphosphino)-ferrocene]-dichloropalladium(II)—DCM complex, and in the presence of a suitable base such as $NaHCO_3$ heating for a suitable period of time that allows the completion of the reaction, for example at 175° C. for 20 minutes under microwave irradiation. In reaction scheme (10), variable $R^1$ is defined as in Formula (I).

Reaction Scheme 10

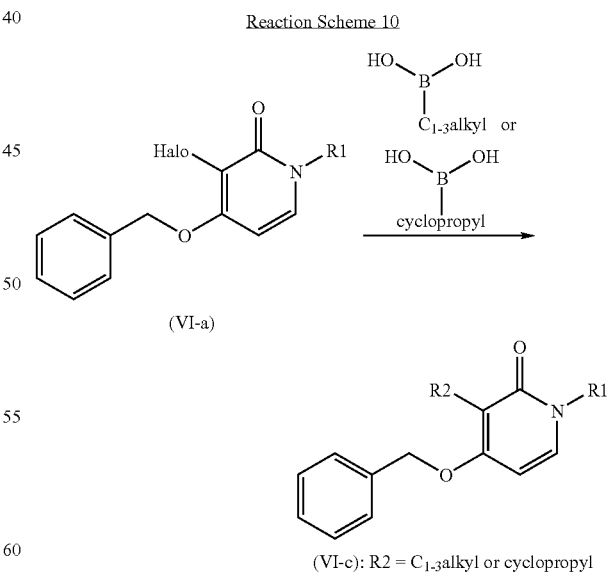

Experimental Procedure 11

Intermediates of Formula (III) can be prepared by art known procedures by reacting an intermediate of Formula (IX) with a suitable boron source such as, for example, bis(pinacolato)diboron in the presence of a Palladium catalyst such as, for example, 1,1'-bis(diphenylphosphino)ferrocene-palladium(II) dichloride in a inert solvent such as, for example, dichloromethane, in the presence of a suitable salt such as, for example, potassium acetate at moderately high temperature such as, for example, 110° C. for as for example 16 hours.

Additionally, intermediates of Formula (III) can be prepared by art known procedures of metal-halogen exchange and subsequent reaction with an appropriate boron source from intermediates of Formula (IX). Thus, for example reaction of an intermediate of Formula (IX) with an organolithium compound such as, for example, n-butyllithium at a moderately low temperature such as, for example, −40° C. in an inert solvent such as, for example, THF followed by subsequent reaction with an appropriate boron source such as, for example, trimethoxyborane. In reaction scheme (11), all variables are defined as in Formula (I) and $R^4$ and $R^5$ may be hydrogen or alkyl, or may be taken together to form for example the bivalent radical of formula —CH$_2$CH$_2$—, —CH$_2$CH$_2$CH$_2$—, or —C(CH$_3$)$_2$C(CH$_3$)$_2$—.

Reaction Scheme 11

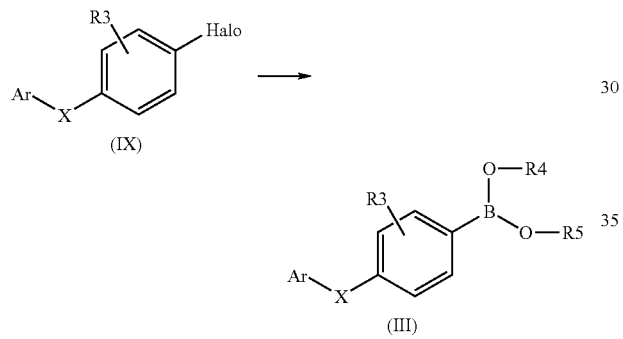

Experimental Procedure 12

Intermediates of Formula (IX) can be prepared by art known procedures by reacting a halogenated intermediate of Formula (X) with a suitable intermediate of Formula (XI), such as for example 2,3-dimethyl-4-nitro-pyridine-1-oxide, in the presence of a suitable base such as, for example, sodium hydride in a inert solvent such as, for example, dimethylformamide, at moderately high temperature such as, for example, 180° C., either under classical or microwave irradiation heating, for a suitable period of time to ensure completion of the reaction. In reaction scheme (12), all variables are defined as in Formula (I), halogen may be chloro, bromo or iodo and W is a suitable leaving group such as halogen or nitro.

Reaction Scheme 12

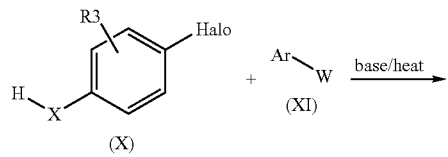

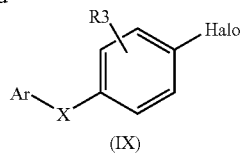

Experimental Procedure 13

Additionally, intermediates of Formula (IX) can be prepared by art known procedures from aniline-like intermediates of Formula (XII) via a Sandmeyer type reaction. In reaction scheme (13), all variables are defined as in Formula (I), halogen may be chloro, bromo or iodo.

Reaction Scheme 13

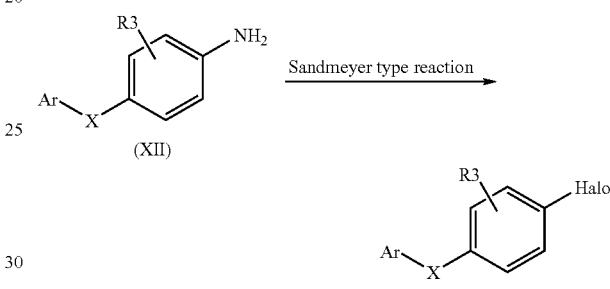

Experimental Procedure 14

Intermediates of Formula (XII) can be prepared by art known procedures from intermediates of Formula (XIII) via reduction of the nitro group to the amino function by art known procedures, such as catalytic hydrogenation or the use of tin(II) chloride dihydrate as a reducing agent. In reaction scheme (14), all variables are defined as in Formula (I).

Reaction Scheme 14

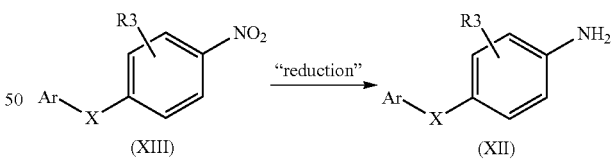

Experimental Procedure 15

Intermediates of Formula (XIII) can be prepared by art known procedures by reacting an intermediate of Formula (XIV) with a suitable intermediate of Formula (XV), in the presence of a suitable base such as, for example, cesium carbonate in an inert solvent such as, for example, tetrahydrofuran, heating at an appropriate temperature and for a suitable period of time that allows the completion of the reaction, either under traditional heating or under microwave irradiation. In reaction scheme (15), all variables are defined as in Formula (I).

Reaction Scheme 15

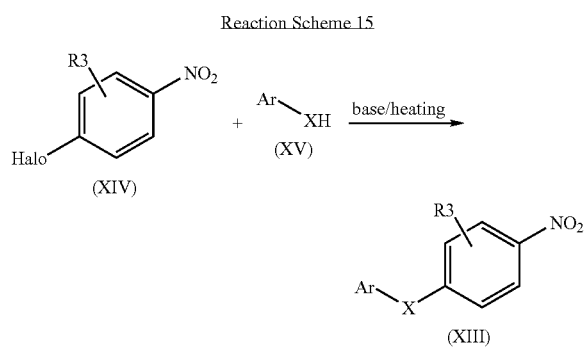

The starting materials according to Formulas (VIII), (X), (XI), (XIV) and (XV) are intermediates that are either commercially available or may be prepared according to conventional reaction procedures well known to anyone skilled in the art.

Pharmacology

The compounds provided in this invention are positive allosteric modulators of metabotropic glutamate receptors, in particular they are positive allosteric modulators of mGluR2. The compounds of the present invention do not appear to bind to the glutamate recognition site, the orthosteric ligand site, but instead to an allosteric site within the seven transmembrane region of the receptor. In the presence of glutamate or an agonist of mGluR2, the compounds of this invention increase the mGluR2 response. The compounds provided in this invention are expected to have their effect at mGluR2 by virtue of their ability to increase the response of such receptors to glutamate or mGluR2 agonists, enhancing the response of the receptor. Hence, the present invention relates to a compound according to the present invention for use as a medicine, as well as to the use of a compound according to the invention or a pharmaceutical composition according to the invention for the manufacture of a medicament for treating or preventing, in particular treating, a condition in a mammal, including a human, the treatment or prevention of which is affected or facilitated by the neuromodulatory effect of allosteric modulators of mGluR2, in particular positive allosteric modulators thereof. The present invention also relates to a compound according to the present invention or a pharmaceutical composition according to the invention for use in the manufacture of a medicament for treating or preventing, in particular treating, a condition in a mammal, including a human, the treatment or prevention of which is affected or facilitated by the neuromodulatory effect of allosteric modulators of mGluR2, in particular positive allosteric modulators thereof. The present invention also relates to a compound according to the present invention or a pharmaceutical composition according to the invention for treating or preventing, in particular treating, a condition in a mammal, including a human, the treatment or prevention of which is affected or facilitated by the neuromodulatory effect of allosteric modulators of mGluR2, in particular positive allosteric modulators thereof.

Also, the present invention relates to the use of a compound according to the invention or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR2.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. treatment, an effective amount of a compound or composition according to the invention.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder Preferably, the central nervous system disorder is a personality disorder selected from the group of obsessive-compulsive personality disorder and schizoid, schizotypal disorder.

Preferably, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of anxiety, schizophrenia, migraine, depression, and epilepsy are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Because such positive allosteric modulators of mGluR2, including compounds of Formula (I), enhance the response of mGluR2 to glutamate, it is an advantage that the present methods utilize endogenous glutamate.

Because positive allosteric modulators of mGluR2, including compounds of Formula (I), enhance the response of mGluR2 to agonists, it is understood that the present invention extends to the treatment of neurological and psychiatric disorders associated with glutamate dysfunction by administering an effective amount of a positive allosteric modulator of mGluR2, including compounds of Formula (I), in combination with an mGluR2 agonist.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

Pharmaceutical Compositions

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof.

The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

As already mentioned, the invention also relates to a pharmaceutical composition comprising the compounds according to the invention and one or more other drugs in the treatment, prevention, control, amelioration, or reduction of risk of diseases or conditions for which compounds of Formula (I) or the other drugs may have utility as well as to the use of such a composition for the manufacture of a medicament. The present invention also relates to a combination of a compound according to the present invention and a mGluR2 orthosteric agonist. The present invention also relates to such a combination for use as a medicine. The present invention also relates to a product comprising (a) a compound according to the present invention, a pharmaceutically acceptable salt thereof or a solvate thereof, and (b) a mGluR2 orthosteric agonist, as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular positive mGluR2 allosteric modulators. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "THF" means tetrahydrofuran; "DMF" means N,N-dimethylformamide; "EtOAc" means ethyl acetate; "DCM" means dichloromethane; "DME" means 1,2-dimethoxyethane; "DCE" means 1,2-dichloroethane; "DIPE" means diisopropylether; "DMSO" means dimethylsulfoxide; "BINAP" means [1,1'-binaphthalene]-2,2'-diylbis[diphenylphosphine]; "DBU" means 1,8-diaza-7-bicyclo[5.4.0]undecene; "M.P." means melting point.

Microwave assisted reactions were performed in a single-mode reactor: Initiator™ Sixty EXP microwave reactor (Biotage AB), or in a multimode reactor: MicroSYNTH Labstation (Milestone, Inc.).

Description 1

4-Benzyloxy-1-cyclopropylmethyl-1H-pyridin-2-one (D1)

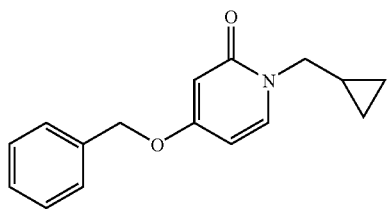

Bromomethyl-cyclopropane (3.68 g, 27.33 mmol) and potassium carbonate (10.3 g, 74.52 mmol) were added to a solution of 4-benzyloxy-1H-pyridin-2-one (5.0 g, 24.84 mmol) in acetonitrile (200 ml) and the mixture was heated at reflux temperature for 16 hours. The reaction mixture was filtered through diatomaceous earth and concentrated in vacuo. The crude residue was then triturated with diethylether to yield pure D1 (6.32 g, 98%) as a white solid.

Description 2

1-Cyclopropylmethyl-4-hydroxy-1H-pyridin-2-one (D2)

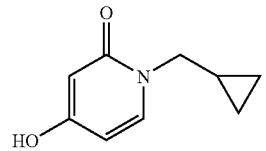

A mixture of intermediate D1 (2.0 g, 7.83 mmol) and a catalytic amount of 10% palladium on activated carbon in ethanol (300 ml) was stirred under a hydrogen atmosphere for two hours. The mixture was filtered through diatomaceous earth and the solvent was evaporated in vacuo to yield intermediate D2 (1.3 g, 100%) that was used without further purification.

Description 3

1-Butyl-3-chloro-4-hydroxy-1H-pyridin-2-one (D3)

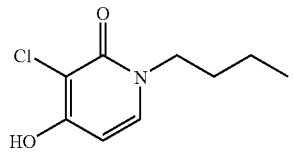

N-Chlorosuccinimide (1.6 g, 11.96 mmol) was added to a solution of 1-butyl-4-hydroxy-1H-pyridine-2-one (2.0 g, 11.96 mmol), which was prepared as described for description D2, in DMF (30 ml). The reaction was stirred at room temperature overnight and then it was concentrated in vacuo. The crude product was purified by column chromatography (silica gel; 0-5% methanol/DCM as eluent) to yield intermediate D3 (2.0 g, 83%).

Description 4

Trifluoromethanesulfonic acid 1-butyl-3-chloro-2-oxo-1,2-dihydropyridin-4-yl ester (D4)

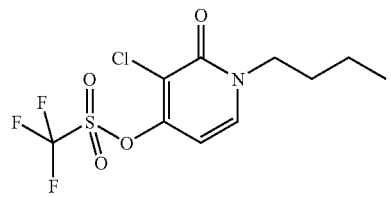

Pyridine (1.60 ml, 19.8 mmol) was added to a cooled (−78° C.) solution of intermediate D3 (2.0 g, 9.92 mmol) in DCM (80 ml). The resulting solution was stirred for 10 minutes. Trifluoromethanesulfonic anhydride (1.90 ml, 10.9 mmol) was added, and the resulting solution was stirred at −78° C. for 3 hours. Then the mixture was warmed to room temperature and it was quenched by the addition of aqueous saturated ammonium chloride, it was diluted with water and extracted with DCM, dried (Na$_2$SO$_4$) and the solvent evaporated in vacuo, yielding intermediate D4 (3.31 g, 100%) as a crude that was used without further purification.

Description 5

Trifluoromethanesulfonic acid 3-chloro-1-cyclopropylmethyl-2-oxo-1,2-dihydro-pyridin-4-yl ester (D5)

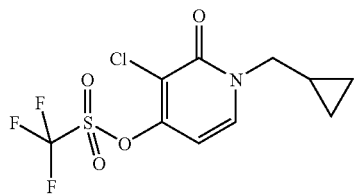

Intermediate D5 was prepared following the same procedure used for the synthesis of intermediate D4, but using intermediate 3-chloro-1-cyclopropylmethyl-4-hydroxy-1H-pyridin-2-one as starting material.

Description 6

4-Benzyloxy-1-cyclopropylmethyl-3-iodo-1H-pyridin-2-one (D6)

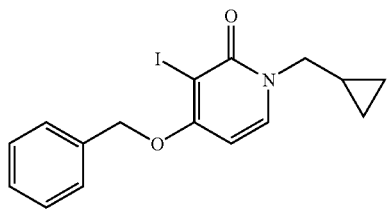

N-Iodosuccinimide (2.64 g, 11.74 mmol) was added to a solution of intermediate D1 (3.0 g, 11.74 mmol) in acetic acid (40 ml). The reaction mixture was stirred at room temperature for 1 hour, after which it was concentrated in vacuo. The residue was purified by column chromatography (silica gel; DCM as eluent) and finally recrystallized from diethyl ether to yield intermediate D6 (4.12 g, 92%) as a solid.

Description 7

4-Benzyloxy-1-cyclopropylmethyl-3-trifluoromethyl-1H-pyridin-2-one (D7)

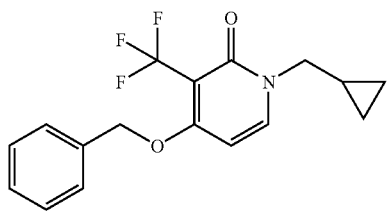

Methyl 2,2-difluoro-2-(fluorosulfonyl)acetate (0.67 ml, 5.24 mmol) and intermediate D6 (1.0 g, 2.63 mmol) were added to a solution of copper(I) iodide (0.99 g, 5.24 mmol) in DMF (30 ml). The mixture was then heated at 100° C. for 5 hours, after which it was filtered through diatomaceous earth and the filtrate was concentrated in vacuo. The residue was purified by column chromatography (silica gel; DCM as eluent) to yield intermediate D7 (0.76 g, 89%).

Description 8

1-Cyclopropylmethyl-4-hydroxy-3-trifluoromethyl-1H-pyridin-2-one (D8)

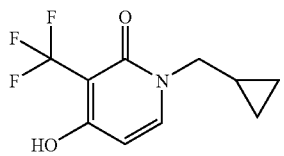

A mixture of intermediate D7 (2.0 g, 6.19 mmol), a catalytic amount of 10% palladium on activated carbon and ethanol (60 ml) was stirred under hydrogen atmosphere for 2 hours. The mixture was filtered through diatomaceous earth and the solvent was evaporated in vacuo to yield crude intermediate D8 (1.45 g, 100%) that was used without further purification.

Description 9

4-Bromo-1-cyclopropylmethyl-3-trifluoromethyl-1H-pyridin-2-one (D9)

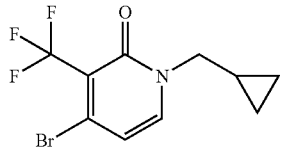

Phosphorus oxybromide (7.03 g, 24.5 mmol) was added to a solution of intermediate D8 (2.60 g, 11.1 mmol) in DMF (50 ml) and the mixture was heated at 110° C. for 1 hour. After cooling in an ice bath the solution was partitioned between water and EtOAc. After three extractions with EtOAc the combined organic fractions were dried (Na$_2$SO$_4$) and the solvent evaporated in vacuo. The crude product was purified by column chromatography (silica gel; DCM as eluent). The desired fractions were collected and evaporated in vacuo to yield intermediate D9 (1.38 g, 42%).

Description 10

4-(4-Bromo-phenoxy)-2-methyl-pyridine (D10)

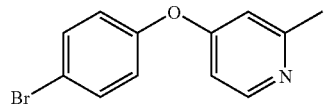

4-Bromophenol (1.0 g, 5.78 mmol) was added to a solution of sodium hydride (0.3 g, 7.51 mmol) in N-methylpyrrolidone (10 ml). After stirring for 10 minutes, 4-chloro-2-methylpyridine (0.96 g, 7.51 mmol) was added. The reaction mixture was heated at 250° C. for 45 minutes under microwave irradiation. After cooling to room temperature the mixture was diluted with diethyl ether and washed with water. The solution was then extracted with additional diethyl ether, the organic layer dried (Na$_2$SO$_4$) and the solvent evaporated in

Description 11

2-Methyl-4-[4-(4,4,5,5-tetramethyl-[1,3,2]diox-aborolan-2-yl)-phenoxy]-pyridine (D11)

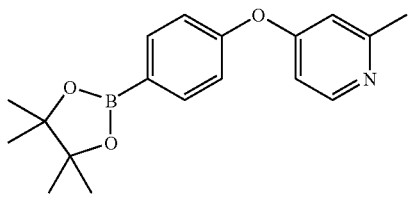

Bis(pinacolato)diboron (0.37 g, 1.45 mmol) and potassium acetate (0.39 g, 4.0 mmol) were added to a solution of intermediate D10 (0.35 g, 1.33 mmol) in dioxane (4 ml) and DMF (1 ml). The mixture was degassed and then [1,1'-bis(diphenylphosphino)-ferrocene]-dichloropalladium(II); complex with DCM (1:1) (0.032 g, 0.04 mmol) was added. The reaction mixture was heated at 150° C. for 10 minutes under microwave irradiation. After cooling to room temperature water was added and the mixture was extracted with EtOAc. The organic fraction was dried ($Na_2SO_4$) and the solvent evaporated in vacuo to afford the desired boronate D11 (0.41 g, 100%) as a crude product that was used without further purification.

Description 12

4-(4-Bromo-3-fluorophenoxy)-2-methylpyridine 1-oxide (D12)

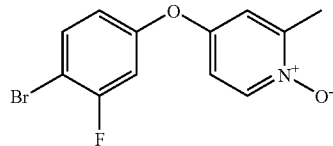

4-Bromo-3-fluorophenol (0.5 g, 2.61 mmol) was added to a solution of sodium hydride (0.115 g, 2.90 mmol) in DMF (5 ml). After stirring for 10 minutes 4-nitro-2-picoline N-oxide (0.37 g, 2.41 mmol) was added. The reaction mixture was heated at 180° C. for 1 hour under microwave irradiation. After cooling to room temperature the mixture was filtered through diatomaceous earth and this was thoroughly washed with EtOAc. The filtrate was washed with water (2×25 ml), the organic fraction was dried ($Na_2SO_4$) and the solvent evaporated in vacuo. The crude product was purified by column chromatography (silica gel; 0-3% methanol/DCM as eluent). The desired fractions were collected and evaporated in vacuo to yield intermediate D12 (0.33 g, 49%).

vacuo. The crude product was purified by column chromatography (silica gel; DCM as eluent). The desired fractions were collected and evaporated in vacuo to yield intermediate D10 (1.34 g, 88%).

Description 13

4-[3-Fluoro-4-(4,4,5,5-tetramethyl-[1,3,2]dioxaborolan-2-yl)-phenoxy]-2-methyl-pyridine (D13)

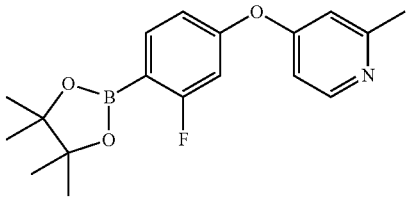

Bis(pinacolato)diboron (1.34 g, 5.31 mmol) and potassium acetate (0.52 g, 5.31 mmol) were added to a solution of intermediate D12 (0.5 g, 1.77 mmol) in dioxane (10 ml) and DMF (3 ml). The mixture was degassed and then [1,1'-bis(diphenylphosphino)-ferrocene]-dichloropalladium(II); complex with DCM (1:1) (0.06 g, 0.07 mmol) was added. The reaction mixture was heated at 150° C. for 10 minutes under microwave irradiation. After cooling to room temperature water was added and the mixture was extracted with EtOAc. The organic fraction was dried ($Na_2SO_4$) and the solvent evaporated in vacuo to afford the desired boronate D13 (0.58 g, 100%) as a crude product that was used without further purification.

Description 14

3-(2-Fluoro-4-nitrophenoxy)-2,6-dimethyl-pyridine (D14)

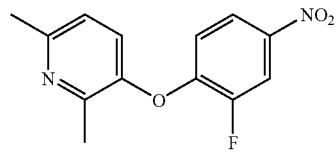

2,6-Dimethyl-pyridin-3-ol (3.0 g, 24.35 mmol) and cesium carbonate (15.87 g, 48.71 mmol) were added to a solution of 3,4-difluoronitrobenzene (3.87 g, 24.35 mmol) in DMF (30 ml). The mixture was heated at 140° C. for 2 hours. After cooling to room temperature it was filtered through diatomaceous earth and the solvent evaporated in vacuo. The crude product was purified by column chromatography (silica gel; 2% methanol/DCM as eluent) to yield intermediate D14 (5.88 g, 92%).

Description 15

4-(2,6-Dimethyl-pyridin-3-yloxy)-3-fluoro-phenylamine (D15)

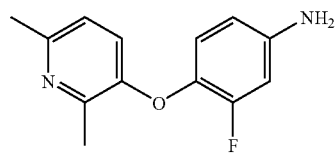

A mixture of intermediate D14 (5.88 g, 22.44 mmol) and 10% Pd/C (~0.5 g, catalytic) in ethanol (200 ml) was stirred under an atmosphere of hydrogen at room temperature for 3 hours. The mixture was filtered through diatomaceous earth and the solvent was evaporated in vacuo to yield intermediate D15 (5.23 g, 100%) that was used without further purification.

Description 16

3-(4-Bromo-2-fluoro-phenoxy)-2,6-dimethyl-pyridine (D16)

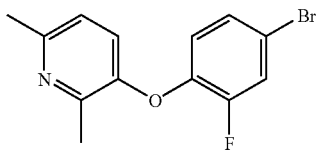

A solution of sodium nitrite (4.57 g, 66.3 mmol) in water (75 ml) was added dropwise (over 45 minutes) to a cooled (at 0° C.) solution of intermediate D15 (7.7 g, 33.2 mmol) in 48% aqueous HBr (75 ml). The reaction mixture was warmed to room temperature and further stirred for 15 minutes, after which it was cooled again to 0° C. and copper(I) bromide (7.31 g, 49.8 mmol) was added portionwise. The mixture was allowed to reach room temperature, stirred for 15 minutes and finally it was heated at 140° C. for 1.5 hours. The reaction mixture was cooled to room temperature and neutralized with an aqueous saturated solution of potassium carbonate. EtOAc was added, the organic layer was separated and washed with brine, dried ($Na_2SO_4$) and the solvent evaporated in vacuo. The crude product was purified by column chromatography (silica gel; 0-10% EtOAc/heptane as eluent). The desired fractions were collected and evaporated in vacuo to yield D16 (8.75 g, 89%) as a pale brown oil.

Description 17

3-[2-Fluoro-4-(4,4,5,5-tetramethyl-[1,3,2]dioxaborolan-2-yl)-phenoxy]-2,6-dimethyl-pyridine (D17)

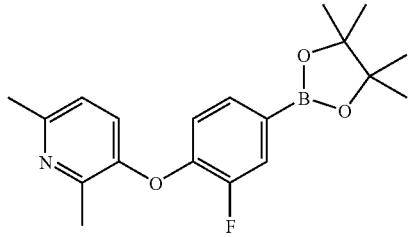

Bis(pinacolato)diboron (3.86 g, 15.2 mmol) and potassium acetate (1.48 g, 15.2 mmol) were added to a solution of intermediate D16 (1.5 g, 5.07 mmol) in dioxane (9 ml) and DMF (3 ml). The mixture was degassed and then [1,1'-bis(diphenylphosphino)-ferrocene]-dichloropalladium(II); complex with DCM (1:1) (0.16 g, 0.20 mmol) was added. The reaction mixture was heated at 150° C. for 10 minutes under microwave irradiation. After cooling to room temperature water was added and the mixture was extracted with EtOAc. The organic fraction was dried ($Na_2SO_4$) and the solvent evaporated in vacuo to afford the desired boronate D17 (1.74 g, 100%) as a crude that was used without further purification.

Description 18

3-(3-Fluoro-4-nitrophenoxy)-2,6-dimethyl-pyridine (D18)

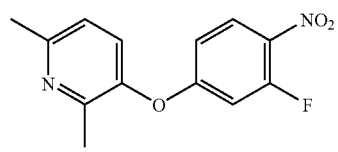

This intermediate was prepared following the same procedure as that described above for D14, but starting from 2,4-difluoronitrobenzene (3.87 g, 24.35 mmol) and using THF as solvent and refluxing the reaction mixture for 12 hours. After purification by column chromatography intermediate D18 (6.18 g, 96%) was obtained.

Description 19

4-(2,6-Dimethyl-pyridin-3-yloxy)-2-fluoro-phenylamine (D19)

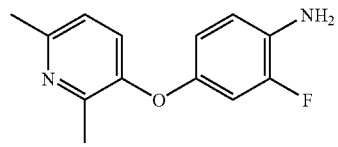

This intermediate was obtained following the same procedure as that described above for D15, but using D18 (6.18 g, 23.58 mmol) as starting material. The isolated intermediate D19 (5.47 g, 100%) was used as such without further purification.

Description 20

3-(4-Bromo-3-fluoro-phenoxy)-2,6-dimethyl-pyridine (D20)

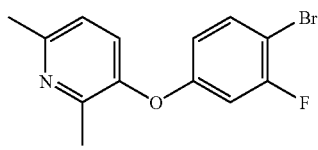

This intermediate was obtained following the same procedure as that described above for D16, but using D19 (4.4 g, 18.9 mmol) as starting material. Intermediate D20 (4.42 g, 79%) was isolated as a pale brown oil.

Description 21

3-[3-Fluoro-4-(4,4,5,5-tetramethyl-[1,3,2]dioxaborolan-2-yl)-phenoxy]-2,6-dimethyl-pyridine (D21)

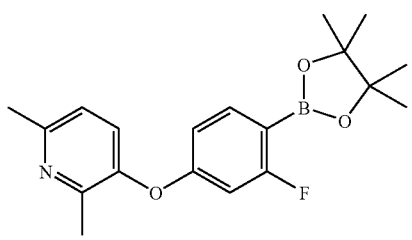

This intermediate was obtained following the same procedure as that described above for D17, but using D20 (1.0 g, 3.37 mmol) as starting material, and heating at 150° C. for 40 minutes instead of 10 minutes. The isolated intermediate D21 (2.19 g, 100%) was used as such without further purification.

Description 22

4-(4-Bromo-2-fluoro-phenoxy)-2,6-dimethyl-pyridine (D22)

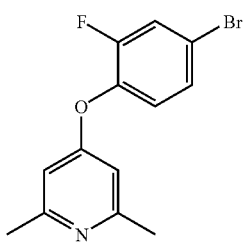

A mixture of 4-bromo-2,6-dimethyl-pyridine (1 g, 5.4 mmol), 4-bromo-2-fluoro-phenol (0.59 g, 5.4 mmol) and potassium carbonate (0.89 g, 6.4 mmol) in xylenes (2 ml) was heated at 150° C. (oil bath temperature) into a sealed tube for 48 hours. After cooling to room temperature the mixture was diluted with EtOAc and filtered through a diatomaceous earth pad. The filtrate was evaporated till dryness and the crude product thus obtained was purified by column chromatography (silica gel; DCM to DCM/EtOAc up to 10% as eluent). The desired fractions were collected and evaporated in vacuo to yield intermediate D22 (1.28 g, 80%).

Description 23

4-[2-Fluoro-4-(4,4,5,5-tetramethyl-[1,3,2]dioxaborolan-2-yl)-phenoxy]-2,6-dimethyl-pyridine (D23)

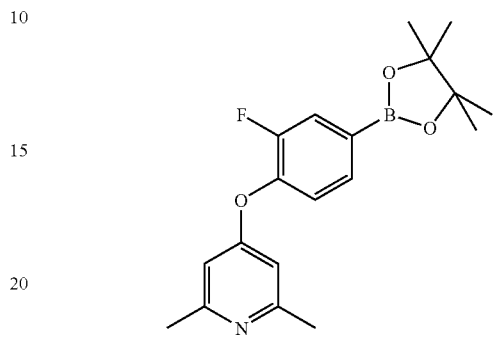

Bis(pinacolato)diboron (1.286 g, 5.06 mmol) and potassium acetate (0.994 g, 10.13 mmol) were added to a solution of intermediate D22 (1 g, 3.37 mmol) in 1,4-dioxane (10.8 ml) and DMF (1.2 ml). The mixture was degassed and then [1,1'-bis(diphenylphosphino)-ferrocene]-dichloropalladium (II)—complex with DCM (1:1) (0.0827 g, 0.101 mmol) was added. The reaction mixture was heated at 150° C. for 10 minutes under microwave irradiation. After cooling to room temperature water was added and the mixture was extracted with EtOAc. The organic fraction was dried (Na$_2$SO$_4$) and the solvent evaporated in vacuo to afford the desired boronate D23 (1.15 g, 100%) as a crude that was used without further purification.

Description 24

4-(4-Hydroxy-phenoxy)-benzoic acid methyl ester
4-(4-Hydroxy-phenoxy)-benzoic acid methyl ester (D24)

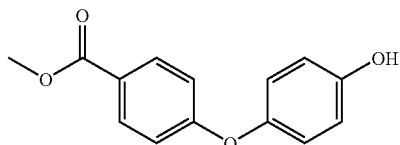

Boron fluoride-dimethyl sulfide complex [CAS: 353-43-5] (15.64 ml, 148.67 mmol) was added dropwise to a stirred solution of methyl 4-(4'-methoxyphenoxy)benzoate [CAS: 38342-84-6] (1.28 g, 4.9 mmol) in DCM (100 ml) cooled in an ice-water bath under nitrogen atmosphere. The resulting mixture was stirred for 5 hours. The reaction mixture was washed with water and then extracted with DCM. The organic layer was separated and dried (Na$_2$SO$_4$) and the solvent was evaporated till dryness. The residue was purified by column chromatography (silica gel; 0-10% EtOAc/DCM as eluent).

The desired fractions were collected and evaporated in vacuo to yield intermediate D24 (0.89 g, 74%).

Description 25

4-(4-Trifluoromethanesulfonyloxy-phenoxy)-benzoic acid methyl ester (D25)

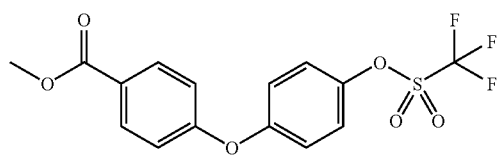

Trifluoromethanesulfonic anhydride (0.92 ml, 5.46 mmol) was added dropwise to a cooled (−78° C.) solution of intermediate D24 (0.89 g, 3.64 mmol) and triethylamine (1.01 ml, 7.29 mmol) in DCM (40 ml). The resulting reaction mixture was further stirred allowing it to warm to room temperature for 1 hour. The mixture was washed with water and the organic layer was separated and dried ($Na_2SO_4$) and the solvent was evaporated till dryness. The residue was purified by column chromatography (silica gel; DCM as eluent). The desired fractions were collected and evaporated in vacuo to yield intermediate D25 (1.25 g, 91%).

Description 26

4-[4-(4,4,5,5-Tetramethyl-[1,3,2]dioxaborolan-2-yl)-phenoxy]-benzoic acid methyl ester (D26)

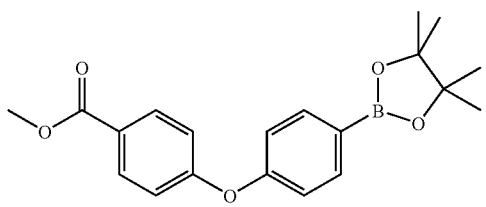

Under nitrogen atmosphere, a mixture of intermediate D25 (0.80 g, 2.12 mmol), bis(pinacolato)diboron (1.35 g, 5.31 mmol), potassium acetate (0.835 g, 8.5 mmol) and [1,1'-bis(diphenylphosphino)-ferrocene]-dichloropalladium(II)-complex with DCM (1:1) (0.10 g, 0.127 mmol) in deoxygenated dioxane (9 ml) and deoxygenated DMF (1 ml) was heated at 150° C. for 40 minutes under microwave irradiation. After cooling to room temperature the mixture was diluted with EtOAc and filtered through celite. The filtrate was washed with water and brine, the organic layer was dried ($Na_2SO_4$) and the solvent was evaporated till dryness, to afford the desired boronate D26 (2.49 g, 100%) as a crude that was used without further purification.

Description 27

4-[4-(1-Butyl-3-chloro-2-oxo-1,2-dihydro-pyridin-4-yl)-phenoxy]-benzoic acid methyl ester (D27)

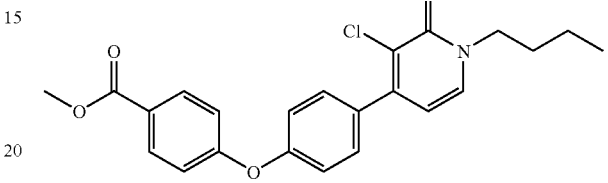

Under nitrogen atmosphere, a mixture of intermediate D26 (1.77 g, 1.5 mmol), intermediate D4 (0.5 g, 1.5 mmol), tetrakis(triphenylphosphine)palladium(0) (0.17 g, 0.15 mmol) and $NaHCO_3$ (6 g, excess) in deoxygenated dioxane (6 ml) was heated at 140° C. for 10 minutes under microwave irradiation. After cooling to room temperature the mixture was diluted with EtOAc and filtered through celite. The filtrate was washed water, then with brine and the organic layer was dried ($Na_2SO_4$) and the solvent was evaporated till dryness. The crude residue was purified by column chromatography (silica gel; 40% EtOAc/heptane as eluent). The desired fractions were collected and evaporated in vacuo and the residue was purified again by column chromatography (silica gel; 20-30% EtOAc/heptane as eluent). The desired fractions were collected and evaporated in vacuo to yield intermediate D27 (0.25 g, 40%) as an amorphous solid.

Description 28

2-[4-(4-Bromo-phenoxy)-phenyl]-propan-2-ol (D28)

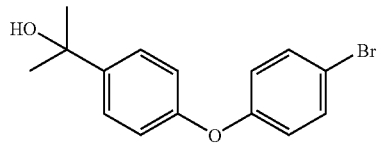

A 1.4 M solution of methylmagnesium bromide in THF (7.36 ml; 10.304 mmol) was added to a stirred solution of 4'-(4-bromophenoxy)acetophenone (1 g, 3.435 mmol; [CAS: 54916-27-7]) in THF (40 ml) at 0° C. under a nitrogen atmosphere. The reaction mixture was stirred for 3 hours. The reaction was quenched by the addition of an aqueous solution of saturated ammonium chloride and extracted with EtOAc. The combined organic extracts were dried ($Na_2SO_4$) and the solvent was evaporated to dryness. The crude residue was purified by column chromatography (silica gel; DCM as eluent). The desired fractions were collected and evaporated in vacuo to yield intermediate D28 (0.8 g, 75%).

Description 29

2-{4-[4-(4,4,5,5-Tetramethyl-[1,3,2]dioxaborolan-2-yl)-phenoxy]-phenyl}-propan-2-ol (D21)

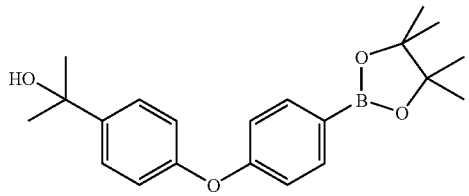

Following the procedure of Description 17, intermediate D28 (0.5 g, 1.628 mmol) was heated at 150° C. for 15 minutes. The crude residue was purified by column chromatography (silica gel; DCM as eluent). The desired fractions were collected and evaporated in vacuo to yield intermediate D29 (0.48 g, 83%).

Example 1

1-Butyl-3-chloro-4-[4-(2-methylpyridin-4-yloxy)-phenyl]-1H-pyridin-2-one (E1)

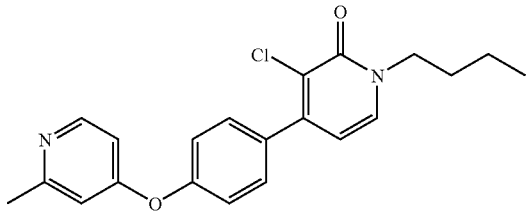

A mixture of intermediate D4 (0.42 g, 1.33 mmol), intermediate D11 (0.41 g, 1.33 mmol), catalyst tetrakis(triphenylphosphine)palladium(0) (0.15 g, 0.13 mmol) and NaHCO$_3$ (3 g, excess) in dioxane (3 ml) was heated at 150° C. for 10 minutes under microwave irradiation. After cooling to room temperature the reaction mixture was filtered through diatomaceous earth and the solvent evaporated in vacuo after washing with more dioxane. The crude product was purified by column chromatography (silica gel; 0-3% methanol/DCM as eluent). The desired fractions were collected and evaporated in vacuo to yield compound E1 (0.04 g, 8%) as an amorphous solid.

Example 2

1-Butyl-3-chloro-4-[2-fluoro-4-(2-methylpyridin-4-yloxy)-phenyl]-1H-pyridin-2-one (E2)

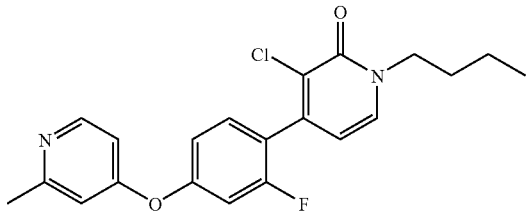

A mixture of intermediate D4 (1.0 g, 3.3 mmol), intermediate D13 (0.58 g, 1.77 mmol), catalyst tetrakis(triphenylphosphine)palladium(0) (0.2 g, 0.17 mmol) and NaHCO$_3$ (6 g, excess) in dioxane (6 ml) was heated at 150° C. for 10 minutes under microwave irradiation. After cooling to room temperature the reaction mixture was filtered through diatomaceous earth and the solvent evaporated in vacuo after washing with more dioxane. The crude product was purified by column chromatography (silica gel; 0-3% methanol/DCM as eluent). The desired fractions were collected and evaporated in vacuo to yield compound E2 (0.051 g, 7.5%) as an amorphous solid.

Example 3

3-Chloro-1-cyclopropylmethyl-4-[4-(2,6-dimethylpyridin-3-yloxy)-3-fluoro-phenyl]-1H-pyridin-2-one (E3)

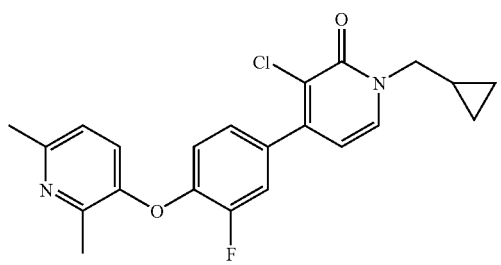

A mixture of intermediate D5 (0.23 g, 0.69 mmol), intermediate D17 (0.27 g, 0.79 mmol), catalyst tetrakis(triphenylphosphine)palladium(0) (0.04 g, 0.035 mmol) and NaHCO$_3$ (6 g, excess) in dioxane (6 ml) was heated at 150° C. for 10 minutes under microwave irradiation. After cooling to room temperature the reaction mixture was filtered through diatomaceous earth and the solvent evaporated in vacuo after washing with more dioxane. The crude residue was purified by column chromatography (silica gel; 2% ammonia in methanol (7M)/DCM as eluent). The desired fractions were collected and evaporated in vacuo to yield compound E3 (0.037 g, 13.5%) as a white solid.

Melting point: 143.4° C.

Example 4

4-[4-(1-Butyl-3-chloro-2-oxo-1,2-dihydro-pyridin-4-yl)-phenoxy]-benzoic acid (E4)

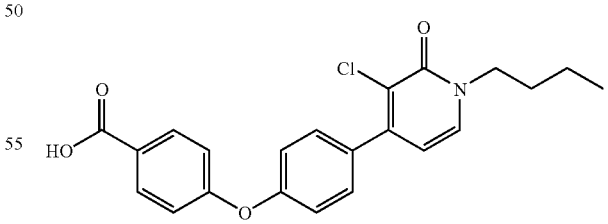

A solution of lithium hydroxide (0.044 g, 1.82 mmol) in water (4 ml) was added dropwise to a solution of intermediate D27 (0.25 g, 0.61 mmol) in dioxane (7 ml) stirred at room temperature. The mixture was then stirred at 80° C. for 2 hours. The cooled crude reaction mixture was acidified with an aqueous 1N HCl solution and it was extracted with EtOAc. The organic layer was separated and dried (Na$_2$SO$_4$) and the solvent was evaporated till dryness. The residue was purified by column chromatography (silica gel; 0-20% methanol/DCM as eluent). The desired fractions were collected and evaporated in vacuo affording a solid, which was washed with diethyl ether to yield compound E4 (0.12 g, 48%) as a white solid.

Melting point: 280.3° C.

Example 5

1-Cyclopropylmethyl-4-[4-(2,6-dimethyl-pyridin-4-yloxy)-3-fluoro-phenyl]-3-trifluoromethyl-1H-pyridin-2-one (E5)

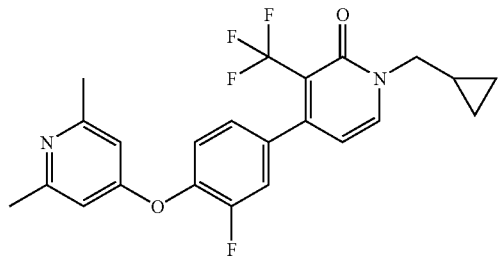

A mixture of intermediate D9 (0.035 g, 0.12 mmol), intermediate D23 (0.046 g, 0.14 mmol), catalyst tetrakis(triphenylphosphine)palladium(0) (0.015 g, 0.014 mmol) and $NaHCO_3$ (1 g, excess) in dioxane (1 ml) was heated at 150° C. for 10 minutes under microwave irradiation. After cooling to room temperature the reaction mixture was filtered through diatomaceous earth and the solvent evaporated in vacuo after washing with more dioxane. The crude residue was purified by column chromatography (silica gel; 0-3% methanol/DCM as eluent). The desired fractions were collected and evaporated in vacuo to yield compound E5 (0.02 g, 38%) as a white solid.

Melting point: 161.8° C.

Compounds E6-E38 (Table 1) were prepared in a similar manner as the five examples describe above, using the appropriate starting materials. Anyone skilled in the art would know how to synthesize all other appropriate starting materials following similar synthetic procedures as those descriptions above.

5 Physico-Chemical Data

LCMS—General Procedure

The HPLC measurement was performed using a HP 1100 from Agilent Technologies comprising a pump (quaternary or binary) with degasser, an autosampler, a column oven, a diode-array detector (DAD) and a column as specified in the respective methods below. Flow from the column was split to a MS spectrometer. The MS detector was configured with an electrospray ionization source. Nitrogen was used as the nebulizer gas. The source temperature was maintained at 140° C. Data acquisition was performed with MassLynx-Openlynx software.

LCMS Method

In addition to the general procedure: Reversed phase HPLC was carried out on an XDB-C18 cartridge (1.8 µm, 2.1×30 mm) from Agilent, with a flow rate of 1 ml/min, at 60° C. The gradient conditions used are: 90% A (0.5 g/l ammonium acetate solution), 5% B (acetonitrile), 5% C (methanol) to 50% B and 50% C in 6.5 minutes, to 100% B at 7 minutes and equilibrated to initial conditions at 7.5 minutes until 9.0 minutes. Injection volume 2 µl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV and the cone voltage was 20 V. Leucine-Enkephaline was the standard substance used for the lock mass calibration.

Melting Points

For a number of compounds, melting points were determined in open capillary tubes on a Mettler FP62 apparatus. Melting points were measured with a temperature gradient of 3 or 10° C./minute. Maximum temperature was 300° C. The melting point was read from a digital display and were obtained with experimental uncertainties that are commonly associated with this analytical method.

TABLE 1

| Ex. | Ar | R1 | R2 | R3 | Salt | Melting Point (° C.) | MH+ | RT (min) |
|---|---|---|---|---|---|---|---|---|
| E1 | (2-methylpyridin-4-yl) | n-butyl | Cl | H | | n.d. | 369 | 4.33 |
| E2 | (2-methylpyridin-4-yl) | n-butyl | Cl | 2'-F | | n.d. | 387 | 4.33 |
| E3 | (2,6-dimethylpyridin-3-yl) | cyclopropylmethyl | Cl | 3'-F | | 143.4 | 399 | 4.38 |

TABLE 1-continued
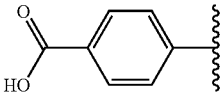
| Ex. | Ar | R1 | R2 | R3 | Salt | Melting Point (° C.) | MH+ | RT (min) |
|---|---|---|---|---|---|---|---|---|
| E4 | 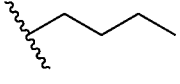 | 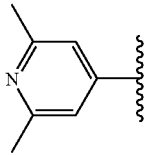 | Cl | H | | 280.3 | 398 | 3.14 |
| E5 | 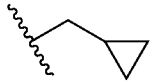 | 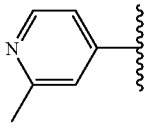 | CF₃ | 3'-F | | 161.8 | 433 | 4.45 |
| E6 | 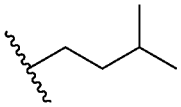 | 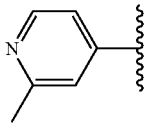 | Cl | H | | n.d. | 383 | 4.64 |
| E7 | 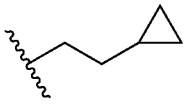 | 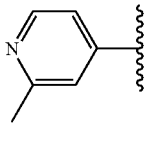 | Cl | H | | n.d. | 381 | 4.32 |
| E8 | 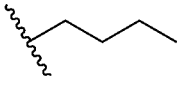 | 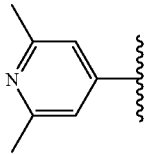 | Cl | 3'-F | | decomposes | 387 | 4.36 |
| E9 | 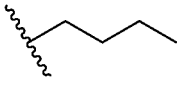 | 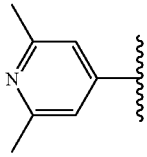 | Cl | 3'-F | | n.d. | 401 | 4.60 |
| E10 | 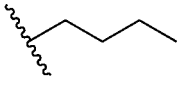 | 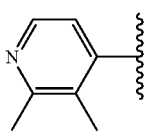 | Cl | 2'-F | | n.d. | 401 | 4.59 |
| E11 | 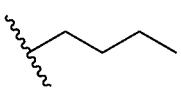 | 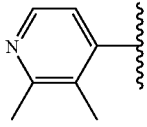 | Cl | 2'-F | | n.d. | 401 | 4.64 |
| E12 | 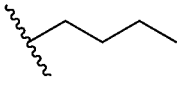 | | Cl | 3'-F | | n.d. | 401 | 4.68 |

TABLE 1-continued
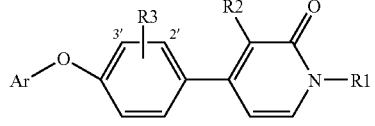
| Ex. | Ar | R1 | R2 | R3 | Salt | Melting Point (° C.) | MH+ | RT (min) |
|---|---|---|---|---|---|---|---|---|
| E13 | 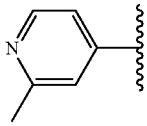 | 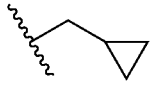 | Cl | H | | decomposes | 367 | 4.10 |
| E14 | 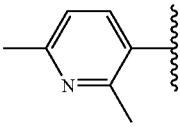 | 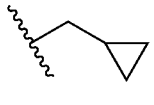 | Cl | H | | 151.8 | 381 | 4.34 |
| E15 | 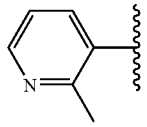 | 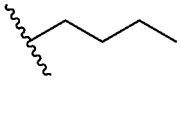 | Cl | 3'-Cl | | n.d. | 403 | 4.66 |
| E16 | 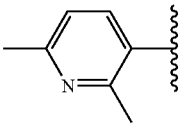 | 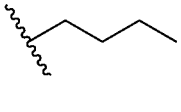 | Cl | H | | n.d. | 383 | 4.63 |
| E17 | 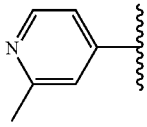 | 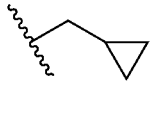 | Cl | 3'-Cl | | 120.8 | 401 | 4.35 |
| E18 | 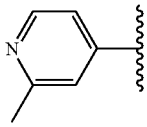 | 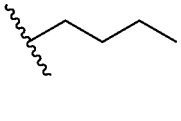 | Cl | 3'-Cl | | decomposes | 403 | 4.62 |
| E19 | 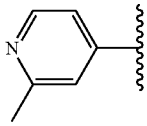 | 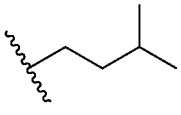 | Cl | 3'-Cl | | 103.8 | 417 | 4.93 |
| E20 | 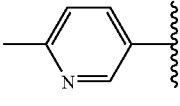 | 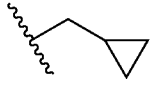 | Cl | 3'-Cl | | 111.8 | 401 | 4.44 |
| E21 | 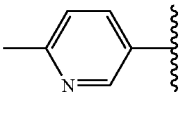 | 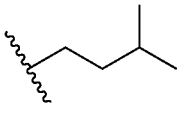 | Cl | 3'-Cl | | 96.1 | 417 | 4.99 |
| E22 | 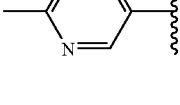 |  | Cl | 3'-Cl | | 79.7 | 403 | 4.70 |

TABLE 1-continued

| Ex. | Ar | R1 | R2 | R3 | Salt | Melting Point (° C.) | MH+ | RT (min) |
|---|---|---|---|---|---|---|---|---|
| E23 | 2-methylpyridin-3-yl | cyclopropylmethyl | Cl | 3'-Cl | | n.d. | 401 | 4.37 |
| E24 | 2-methylpyridin-3-yl | cyclopropylmethyl | Cl | H | | 126.2 | 367 | 4.11 |
| E25 | 2-methylpyridin-3-yl | butyl | Cl | H | | n.d. | 369 | 4.31 |
| E26 | 2-methylpyridin-4-yl | 2-cyclopropylethyl | Cl | 2'-F | | n.d. | 399 | 4.30 |
| E27 | 2-methylpyridin-4-yl | cyclopropylmethyl | Cl | 3'-F | | 176.0 | 385 | 4.09 |
| E28 | 2-methylpyridin-4-yl | cyclopropylmethyl | Cl | 2'-F | | 131.8 | 385 | 4.10 |
| E29 | 2-methylpyridin-3-yl | pent-2-yl | Cl | 2'-F | | 108.4 | 387 | 4.19 |
| E30 | 2,6-dimethylpyridin-3-yl | pent-2-yl | Cl | 3'-F | | n.d. | 401 | 4.65 |
| E31 | 2,6-dimethylpyridin-4-yl | cyclopropylmethyl | Cl | 3'-F | | 161.6 | 399 | 4.32 |

TABLE 1-continued

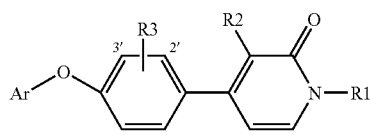

| Ex. | Ar | R1 | R2 | R3 | Salt | Melting Point (° C.) | MH+ | RT (min) |
|-----|----|----|----|----|------|---------------------|-----|----------|
| E32 | 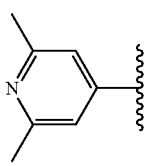 | 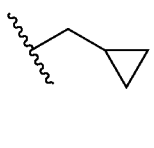 | Cl | 2'-F | | 148.6 | 399 | 4.33 |
| E33 | 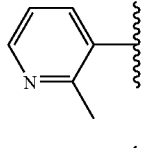 | 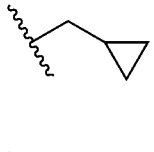 | Cl | 3'-F | | n.d. | 385 | 4.09 |
| E34 | 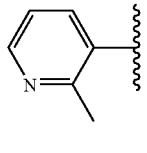 | 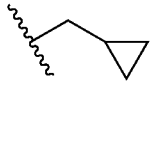 | Cl | 2'-F | | 120.9 | 385 | 3.93 |
| E35 | 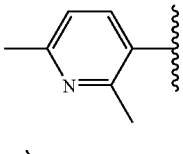 | 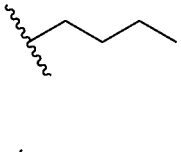 | Cl | 2'-F | •HCl | n.d. | 401 | 4.47 |
| E36 | 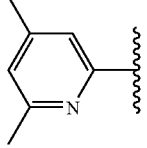 | 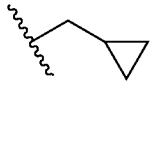 | Cl | 2'-F | | n.d. | 399 | 4.71 |
| E37 | 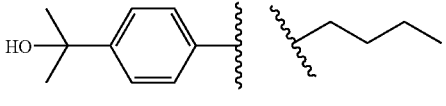 | 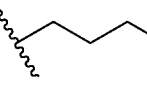 | Cl | H | | n.d. | 412 | 4.70 |
| E38 | 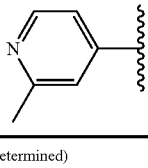 | 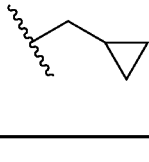 | CF$_3$ | 3'-F | | 203.9 | 419 | 4.28 |

(n.d. means not determined)

D. PHARMACOLOGICAL EXAMPLES

The compounds provided in the present invention are positive allosteric modulators of mGluR2. These compounds appear to potentiate glutamate responses by binding to an allosteric site other than the glutamate binding site. The response of mGluR2 to a concentration of glutamate is increased when compounds of Formula (I) are present. Compounds of Formula (I) are expected to have their effect substantially at mGluR2 by virtue of their ability to enhance the function of the receptor. The behaviour of positive allosteric modulators tested at mGluR2 using the [$^{35}$S]GTPγS binding assay method described below and which is suitable for the identification of such compounds, and more particularly the compounds according to Formula (I), are shown in Table 4.

[$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein a subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the agonist can be determined. mGluR2 receptors are shown to be preferentially coupled to Gαi-protein, a preferential coupling for this method, and hence it is widely used to study receptor activation of mGluR2 receptors both in recombinant cell lines and in tissues (Schaffhauser et al 2003, Pinkerton et al, 2004, Mutel et al (1998) Journal of Neurochemistry. 71:2558-64; Schaffhauser et al (1998) Molecular Pharmacology 53:228-33). Here we describe the use of the [$^{35}$S]GTPγS binding assay using membranes from cells transfected with the human mGluR2 receptor and adapted from Schaffhauser et al ((2003) Molecular Pharmacology 4:798-810) for the detection of the positive allosteric modulation (PAM) properties of the compounds of this invention.

Membrane Preparation

CHO-cells were cultured to pre-confluence and stimulated with 5 mM butyrate for 24 hours, prior to washing in PBS, and then collection by scraping in homogenisation buffer (50 mM Tris-HCl buffer, pH 7.4, 4° C.). Cell lysates were homogenized briefly (15s) using an ultra-turrax homogenizer. The homogenate was centrifuged at 23 500×g for 10 minutes and the supernatant discarded. The pellet was resuspended in 5 mM Tris-HCl, pH 7.4 and centrifuged again (30 000×g, 20 min, 4° C.). The final pellet was resuspended in 50 mM HEPES, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 positive allosteric modulatory activity of test compounds in membranes containing human mGluR2 was performed using frozen membranes that were thawed and briefly homogenised prior to pre-incubation in 96-well microplates (15 μg/assay well, 30 minutes, 30° C.) in assay buffer (50 mM HEPES pH 7.4, 100 mM NaCl, 3 mM MgCl$_2$, 50 μM GDP, 10 μg/ml saponin,) with increasing concentrations of positive allosteric modulator (from 0.3 nM to 50 μM) and either a minimal pre-determined concentration of glutamate (PAM assay), or no added glutamate. For the PAM assay, membranes were pre-incubated with glutamate at $EC_{25}$ concentration, i.e. a concentration that gives 25% of the maximal response glutamate, and is in accordance to published data (Pin et al. (1999) Eur. J. Pharmacol. 375:277-294). After addition of [$^{35}$S]GTPγS (0.1 nM, f.c.) to achieve a total reaction volume of 200 microplates were shaken briefly and further incubated to allow [$^{35}$S]GTPγS incorporation on activation (30 minutes, 30° C.). The reaction was stopped by rapid vacuum filtration over glass-fibre filter plates (Unifilter 96-well GF/B filter plates, Perkin-Elmer, Downers Grove, USA) microplate using a 96-well plate cell harvester (Filtermate, Perkin-Elmer, USA), and then by washing three times with 300 μl of ice-cold wash buffer (Na$_2$PO$_4$.2H$_2$O 10 mM, NaH$_2$PO$_4$.H$_2$O 10 mM, pH=7.4). Filters were then air-dried, and 40 μl of liquid scintillation cocktail (Microscint-O) was added to each well, and membrane-bound [$^{35}$S]GTPγS was measured in a 96-well scintillation plate reader (Top-Count, Perkin-Elmer, USA). Non-specific [$^{35}$S]GTPγS binding is determined in the presence of cold 10 μM GTP. Each curve was performed at least once using duplicate sample per data point and at 11 concentrations.

Data Analysis

The concentration-response curves of representative compounds of the present invention in the presence of added $EC_{25}$ of mGluR2 agonist glutamate to determine positive allosteric modulation (PAM), were generated using the Prism GraphPad software (Graph Pad Inc, San Diego, USA). The curves were fitted to a four-parameter logistic equation (Y=13ottom+(Top-Bottom)/(1+10^(($LogEC_{50}$-X)*Hill Slope) allowing determination of $EC_{50}$ values. The $EC_{50}$ is the concentration of a compound that causes a half-maximal potentiation of the glutamate response. This is calculated by subtracting the maximal responses of glutamate in presence of a fully saturating concentration of a positive allosteric modulator from the response of glutamate in absence of a positive allosteric modulator. The concentration producing the half-maximal effect is then calculated as $EC_{50}$

TABLE 2

Pharmacological data for compounds according to the invention.
All compounds were tested in presence of mGluR2 agonist, glutamate at a predetermined $EC_{25}$ concentration, to determine positive allosteric modulation (GTPγS-PAM). Values shown are averages of duplicate values of 11-concentration response curves, from at least one experiment. All compounds except compound No. 29, 34 and 35 showed a $pEC_{50}$ value of more than 5.0, from 6.05 to 7.40.
The error of determination of a $pEC_{50}$ value for a single experiment is estimated to be about 0.3 log-units.

| Comp. No. | GTPgS - hR2 PAM $pEC_{50}$ |
|---|---|
| 1 | 6.60 |
| 2 | 6.55 |
| 3 | 6.74 |
| 4 | 6.86 |
| 5 | 7.12 |
| 6 | 6.77 |
| 7 | 6.76 |
| 8 | 6.76 |
| 9 | 6.63 |
| 10 | 6.70 |
| 11 | 7.17 |
| 12 | 6.89 |
| 13 | 6.29 |
| 14 | 6.86 |
| 15 | 7.22 |
| 16 | 7.17 |
| 17 | 6.93 |
| 18 | 7.00 |
| 19 | 7.17 |
| 20 | 7.04 |
| 21 | 7.33 |
| 22 | 7.33 |
| 23 | 6.90 |
| 24 | 6.36 |
| 25 | 6.65 |
| 26 | 6.81 |
| 27 | 6.45 |
| 28 | 6.44 |
| 29 | <5.0 |
| 30 | 7.33 |
| 31 | 6.54 |
| 32 | 6.43 |
| 33 | 6.21 |
| 34 | <5.0 |
| 35 | <5.0 |
| 36 | 6.05 |
| 37 | 7.40 |
| 38 | 6.99 |

E. COMPOSITION EXAMPLES

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

1. Tablets

|  |  |
| --- | --- |
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

|  |  |
| --- | --- |
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound having the formula (I)

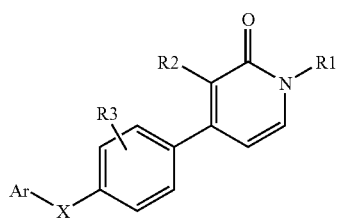

(I)

or a stereochemically isomeric form thereof, wherein $R^1$ is $C_{1-6}$alkyl; or $C_{1-3}$alkyl substituted with $C_{3-7}$cycloalkyl, phenyl, or phenyl substituted with halo, trifluoromethyl or trifluoromethoxy;

$R^2$ is halo, trifluoromethyl, $C_{1-3}$alkyl or cyclopropyl;

$R^3$ is hydrogen or halo;

X is O, S, SO, $SO_2$, or $CF_2$; and

Ar is unsubstituted phenyl; unsubstituted pyridinyl; or phenyl or pyridinyl substituted with one or two substituents selected from the group consisting of halo, $C_{1-3}$alkyl, $C_{1-3}$alkoxy, trifluoromethyl, hydroxy$C_{1-3}$alkyl and $(CH_2)_n$—$CO_2H$, wherein n=0, 1, or 2; or a pharmaceutically acceptable salt thereof, provided that when $R^3$ is 2'-fluoro then Ar is not 3-pyridinyl substituted with one or two $C_{1-3}$alkyl substituents.

2. The compound according to claim 1 wherein $R^1$ is 1-butyl, 2-methyl-1-propyl, 3-methyl-1-butyl, (cyclopropyl)methyl or 2-(cyclopropyl)-1-ethyl;

$R^2$ is chloro or trifluoromethyl;

$R^3$ is hydrogen, chloro or fluoro;

X is O; and

Ar is pyridinyl substituted with at least one methyl, or phenyl substituted with COOH or hydroxy$C_{1-3}$alkyl;

or a pharmaceutically acceptable salt thereof.

3. The compound according to claim 1 wherein $R^1$ is 1-butyl, 3-methyl-1-butyl, (cyclopropyl)methyl or 2-(cyclopropyl)-1-ethyl;

$R^2$ is chloro;

$R^3$ is chloro or fluoro;

X is O; and

Ar is 2-methylpyridin-4-yl, 2-methylpyridin-3-yl or 2,6-dimethylpyridin-4-yl, or a pharmaceutically acceptable salt thereof.

4. A compound according to claim 1 wherein said compound is selected from the group consisting of:

1-Butyl-3-chloro-4-[4-(2-methylpyridin-4-yloxy)-phenyl]-1H-pyridin-2-one

1-Butyl-3-chloro-4-[2-fluoro-4-(2-methylpyridin-4-yloxy)-phenyl]-1H-pyridin-2-one 3-Chloro-1-cyclopropylmethyl-4-[4-(2,6-dimethylpyridin-3-yloxy)-3-fluoro-phenyl]-1H-pyridin-2-one 4-[4-(1-Butyl-3-chloro-2-oxo-1,2-dihydro-pyridin-4-yl)-phenoxy]-benzoic acid 1-Cyclopropylmethyl-4-[4-(2,6-dimethyl-pyridin-4-yloxy)-3-fluoro-phenyl]-3-trifluoromethyl-1H-pyridin-2-one.

5. A pharmaceutical composition comprising a therapeutically effective amount of a compound of claim 1 and a pharmaceutically acceptable carrier or excipient.

6. A compound according to claim 1 for use as a medicament.

* * * * *